(12) United States Patent
Polymeropoulous et al.

(10) Patent No.: US 7,001,720 B1
(45) Date of Patent: Feb. 21, 2006

(54) CLONING OF A GENE MUTATION FOR PARKINSON'S DISEASE

(75) Inventors: Mihael H. Polymeropoulous, Potomac, MD (US); Christian Lavedan, North Potomac, MD (US); Elisabeth Leroy, Washington, DC (US); Robert L. Nussbaum, Chevy Chase, MD (US); William G. Johnson, Short Hills, NJ (US); Roger C. Duvoisin, Sante Fe, NM (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/446,628

(22) PCT Filed: Jun. 25, 1998

(86) PCT No.: PCT/US98/13071

§ 371 (c)(1),
(2), (4) Date: Sep. 19, 2001

(87) PCT Pub. No.: WO98/59050

PCT Pub. Date: Dec. 30, 1998

Related U.S. Application Data

(60) Provisional application No. 60/050,684, filed on Jun. 25, 1997.

(51) Int. Cl.
  C12Q 1/68    (2006.01)
  C07H 21/04   (2006.01)
  C12N 5/00    (2006.01)
  C12N 15/00   (2006.01)

(52) U.S. Cl. ............... 435/6; 435/69.1; 435/320.1; 435/325; 536/23.1; 536/23.5

(58) Field of Classification Search ............ 435/69.1, 435/320.1; 536/23.5; 530/300
See application file for complete search history.

(56) References Cited

U.S. PATENT DOCUMENTS 5,494,794 A   2/1996   Wallace

FOREIGN PATENT DOCUMENTS

WO   WO 9409162 A   4/1994

OTHER PUBLICATIONS

Xi et al. (1996), Genetic Studies in Alzheimer's Disease with an NACP/alpha-Synuclein Polymorphism, Ann. Neur. 40(2): 207-215.*

Bormann et al. (1996), Cloning and Heterologous Expression of the Entire Set of Structural Genes for Nikkomycin Synthesis from *Streptomyces tendae* Tu901 in *Streptomyces lividans*, J. Bacteriology 178(4): 1216-1218.*

Kreissig et al. (1996), Expression of peptides encoded by exons in cloned mammalian DNA, Nuc. Acids Res. 24(21): 4358-4359.*

Xia et al. (1996), NCBI Accession No. AAC02114, NACP gene product.*

Schapira, A.H., "Pathogenesis of Parkinson's Disease;" Bailleres Clinical Neurology, vol. 6, No. 1, Apr. 1997, pp. 15-36.

Jakes, R. et al, "Identification of Two Distinct Synucleins from Human Brain," FEBS Letters, vol. 345, 1994, pp. 27-32.

Ueda, K. et al, "Molecular Cloning of cDNA Encoding an Unrecognized Component of Amyloid in Alzheimer Disease," Proc. Natl. Acad. Sci. USA, vol. 90, 1993, pp. 11282-11286.

Chen, X. et al, "The Human NACP/Alpha-Synuclein Gene: Chromosome Assignment to 4q21.3-q22 adn Taql RFLP Analysis," GENOMICS, vol. 26, No. 2, 1995, pp. 425-427.

Polymeropoulos, M. H. et al, "Mapping of a Gene for Parkinson's Disease to Chromosome 4q21-q23," SCIENCE, vol. 274, 1996, pp. 1197-1199.

Maroteaux, L. and Scheller, R. H., "The Rat Brain Synucleins: Family Of Proteins Transiently Associated With Neuronal Membrane," Molecular Brain Research, vol. 11, 1991, pp. 335-343.

Nussbaum, R.L. et al., "Genetics of Parkinson's Disease," Human Molecular Genetics, vol. 6, No. 10, 1997, pp. 1687-1691.

Geodert, M., "The Awakening of Alpha-Synuclein," NATURE, vol. 388, Jul. 17, 1997, pp. 232-233.

Polymeropoulos, M. H. et al, "Mutation in the Alpha-Synuclein Gene Identified in Families with Parkinson's Disease," SCIENCE, vol. 276, Jun. 27, 1997, pp. 2045-2047.

* cited by examiner

Primary Examiner—Lorraine Spector
Assistant Examiner—Jon M Lockard
(74) Attorney, Agent, or Firm—Venable LLP; Ann S. Hobbs

(57) ABSTRACT

Parkinson's disease (PD) is a common neurodegenrative disorder with a lifetime incidence of approximately 2 percent. It was recently reported that a PD susceptibility gene is located on the long arm of human chromosome four. The present invention reports the subsequent identification of a mutation in the alpha synuclein gene, which codes for a presynaptic protein thought to be involved in neuronal plasticity. The finding of a specific molecular alteration which is causative for PD will permit the detailed understanding of the pathophysiology of the disorder, which will lead to potential therapetuic interventions, as well as a means for diagnosing individuals having an increased risk of developing the disease.

6 Claims, 16 Drawing Sheets

Figure 7

| clone | 5 | 3 | gene |
|---|---|---|---|
| 109979 | T84229 | T88834 | alpha |
| 111088 | T83410 | | alpha |
| 111090 | T83411 | T81593 | alpha |
| 130048 | R11619 | (R19409) | alpha |
| 135534 | R31354 | R32856 | alpha |
| 141246 | R66863 | R67383 | alpha |
| 145594 | R78091 | R77746 | alpha |
| 171906 | H19290 | H19291 | beta |
| 172284 | H19556 | H19474 | beta |
| 172749 | | H19685 | beta |
| 175546 | | H41126 | beta |
| 193174 | H47503 | H47504 | alpha |
| 210768 | H66914 | H66869 | alpha |
| 213616 | H70324 | H70325 | alpha |
| 236027 | H62070 | | alpha |
| 248153 | N53829 | N73325 | alpha |
| 24991 | (T80528) | R39000 | alpha |
| 26298 | R13508 | (R20629) | alpha |
| 265817 | N28661 | N21457 | alpha |
| 266628 | | N22757 | alpha |
| 27342 | | R37173 | alpha |
| 280344 | (N50305) | N47094 | alpha |
| 290894 | | N72005 | alpha |
| 294142 | | N68597 | alpha |
| 307787 | W21278 | | alpha |
| 340635 | W56712 | W56757 | alpha |
| 340683 | W55988 | W56276 | alpha |
| 346647 | W94390 | W74638 | alpha |
| 346796 | W79585 | W79784 | alpha |
| 359349 | AA010546 | AA010547 | alpha |
| 364632 | AA022809 | AA022690 | alpha |
| 39915 | | R50455 | beta |
| 40764 | R56327 | R56245 | alpha |
| 45086 | H06908 | H08824 | alpha |
| 46607 | H10267 | H10213 | alpha |
| 49811 | H29080 | H28976 | alpha |
| 50202 | | H17962 | beta |
| 50470 | | H16811 | beta |
| 66473 | R16018 | R16119 | alpha |
| 667794 | AA258686 | AA258608 | alpha |
| 69907 | T48654 | T48655 | alpha |
| 72391 | AA394097 | AA293803 | gamma |
| 739009 | AA421586 | | beta |
| 739014 | (AA42185) | AA421567 | beta |
| 771303 | | AA443638 | gamma |
| 2-4 | | L36675 | alpha |
| 2-5 | | L36674 | alpha |
| c-01f06 | | F01363 | alpha |
| c-1rb08 | F03254 | F06981 | alpha |
| c-2td12 | F08836 | F11169 | alpha |
| c-28f08 | F03751 | F07521 | alpha |
| cDNA | S69965 | | beta |
| EST01420 (HRBAA27) | M78265 | | gamma |
| EST19193 | AA317129 | | beta |
| EST22040 | AA319774 | | alpha |

Figure 7 cont.

| | | | |
|---|---|---|---|
| EST26845 | T28079 | | beta |
| EST31489 | AA328063 | | alpha |
| EST68G11 | W22518 | | gamma |
| F1-825D | R29481 | | alpha |
| GBN-129D09 | D81090 | | beta |
| hbc590 | T11070 | | alpha |
| HIBBA65 | T08213 | T08212 | alpha |
| | HR70E3R | HR70E3F | alpha |
| HSNACP0 | | U46896-46901 | alpha |
| KK1311 | N83633 | | alpha |
| | | D318839 | alpha |
| | | L08850 | alpha |
| | T28735 | | alpha |
| | Z20502 | | alpha |

Figure 8

```
          10        20        30        40        50        60        70
CCGCCGCAGCCGCCGCTCCATCCCCAGCCCCGGCCCCGCATCCGGTTTGGAAGGGGGCTGCAAGTTTGCA  70
AGGGGCCCGGGAXAAAAAXCGAGCAGTGGCCCTTCCCGCGTCCCCAGGGTTTCAAGGGACGCTAGGAXTXf 140
TCCGCGGCCCTGGAGGTTCGCACTGGGGAGTGGGGTGAGATGGGGGAAAGCGGGAGGGGGCTCAGGGTC  210
CAGAAGGGCXCCGCGGTCTCGGGAGTAGGGGGGCATXTGCGTCCCGCGGGAGGGGCTGGGGTGAGAGTGC 280
GGGGCCAGTGCACCGGTGCCCGTGTATCGCCCTCCCCAGGCCGCCAGGATGGACGTGTTCATGAAGGGCC 350
          360       370       380       390       400       410       420
TGTCCATGGCCAAGGAGGGCGTTGTGGCAGCCGCGGAGAAAACCAAGCAGGGGGTCACCGAGGCGGCGGA  420
GAAGACCAAGGAGGGCGTCCTCTACGTCGGTGGGCXGGGGGCXGGGTTTCTGGGGCTGCAGGGCTGGGGG 490
TCCCCCTACAGTGTGGAGCTGGGGCCGGGTCCCGGGGAGGGGGGTTCTGGGCAAGATAATATXAXTCAGC 560
AGATGGGGCXAGGTCAXCAXGGGTCATAAGGGACATACCCAXCCCATAGAAXCCTGGGTCTGTATCCGGA 630
AATGGGGACACGGGGCGGGCTGATGAGGTGGGGGGCTCCAXCTGAAAGGCCAGGGACCAXTGCAXTXATA 700
          710       720       730       740       750       760       770
AAAXCACACAXCCTCCTTTTTTCTIATCTTTTTTTACCATTATTAATAGTTATCTGGTGTTGAACACTTTCT 770
GTATGCCAAGTACTGGGTAAAATGTCATAACATCCATTTCCTCATGTAATGCTTCCGCCCATTCTACAGG 840
TAAGGGAAACTGGGCTTCCCATTGGTAGXTAAATTTTAGGTTCAGAAAGGCTTGAATTGAATGTCAGTTC 910
AGCCAATTTCTTAGTGGTGGAACCAAACTGAGTTCCATCCGTGAAACGGGGACAATAACAGCACCCGCTT 980
CCCAGGGCTGGGGAAAAGTGAAGTGCAGCGGGGCAGGCAGGGACTTGACACAGCACTGGCCCTCAGCCA 1050
          1060      1070      1080      1090      1100      1110      1120
ACATCCACTAGAGGGGTGGGGTATCGCATCAGGTGGGAGAGAACTGCAACCCTTGCAGACAGAGGTGTGG 1120
GGCCCAGTGCAGTGATAAGACGGGGGTTAACATGGGGGTGCAGGTTGTAGGATXTGGGGACCCAAGGAGG 1190
CAGTGACGGGGCCAGGATGCCCACTCTGTAATCACCATGCTGTGCTGGAGTTTCTGTTCCCfCAGCGCAG 1260
AGTCCTTAAATGTGCCGCTTTTTCTXCCCIGCAGGAAGCAAGACCCGAGAAGGTGTGGTACAAGGTGTGG 1330
CITCAGGTACTAGCCCAGCCCTGGCACCAGCCCTTCTCTCAHTTAGGCGGATGATCTGGCCGGGAACCAG 1400
          1410      1420      1430      1440      1450      1460      1470
AGGGCGGGGGCGGGGGAGACTCCCAAGGCTTCTGCGGGAATGCTCCGTGGGGAGGGCAGGCCCTGGGATA 1470
CTACAAGGCAGGGCATCGGTGTTTCCCCCTGGCTCCCAAACCCCTTCCTCAACCCCCTCCCTGCTCCAGT 1540
GGCTGAAAAAACCAAGGAACAGGCCTCACATCTGGGAGGAGCTGTGTTCTCTGGGGCAGGGAACATCGCA 1610
GCAGCCACAGGACTGGTGAAGAGGGAGGAATTCCCTACTGATCTGAAGGTAAGCGATCCTTCTGACCCGC 1680
ACATGCAGGCAAACACACACACACACACACACACCXGGCACACAAATAAACCTGTCACCATCCCCG 1750
          1760      1770      1780      1790      1800      1810      1820
CCCCCCTAATCCTGCCACCAGCTTGGAACACAAGCCACTTTGCCTCCCATCCTGCXGGCCCGTGCTAGAC 1820
TCAGCTCAGAATGCATCTGAATAAXGGCGTGCATGGGTGTGACGCTCCCGGTGATGGGGACCCAGACCTG 1890
GCTGTCTGCGTGTATCCTGCTTGCCAGCGTGACCCATATGACTTCTGGCCACGTCTGCATGTGTCAATGA 1960
TTGTTCATTCATTTCTTTTCATTCAACAAATATCCATGCCAXAXCCAGCCCTGTCCTTGAGCTTCCAGXT 2030
CCCTTTCAGCCXAGGGGAGCXTGAGGGTTATTTTTGGGGTCCCGATGCCCAGCACAGAGCCTGACACAAA 2100
          2110      2120      2130      2140      2150      2160      2170
GGATGAGGCATAAGCTGGTGAXTGAGTATCCAAATGGTGGAAGTGTGGAGGXTGCCAGGCATTGGGGGAG 2170
CGGCGTGGAGAGCCAGCTCCCCAATCCATGCTGCCACTTCAACTGTGATTCGGGGGAATTTCCCCCTTCA 2240
CCTCCATCCCACTTCCAAGGCACTCCAAATAAATAACTGAATTAGAAATTATCCTTGTTTTGCCAACCCA 2310
CCCTAGCCTTCCCCACTCCAACCCACCCAAAGCTTACCACTGTGGGAATTTGGGGGGCATCCTGGCTGTC 2380
CTCACGAGTCCTGACCTTTTCTGCCCACAGCCAGAGGAAGTGGCCCAGGAAGCTGCTGAAGAACCACTGA 2450
          2460      2470      2480      2490      2500      2510      2520
TTGAGCCCCTGATGGAGCCAGAAGGGGAGAGTTATGAGGACCCACCCCAGGAGGAATATCAGGAGTATGA 2520
GCCAGAGGCGTAGGGGCCCAGGAGAGCCCCCACCAGCAGCACAATTCTGTCCCTGTCCCTGCCCCGCCCC 2590
CCAGAGCCAGGGCTGTCCTTAGACTCCTTCTCCCCAATCACGAGATCTTCCTTCCGCTCTGAGGCAACCC 2660
CCTCGGAGCCTGTGTTAGTGTCTGTCCATCTGTCTGTCCTACCCGCCCGCGTCCAACCCCGGGGCATGGA 2730
CAGGGCCAGGGTTGCGGTCGCGGCTGGGAGCCTCGCCCCTCCAGTGTTGCCTCCTCCCATCCAGCGTCTG 2800
          2810      2820      2830      2840      2850      2860      2870
CGCG 2804
```

Figure 9

```
              10        20        30        40
   ....|....|....|....|....|....|....|....|
   AGGGAGATCCAGCTCCGTCCTGCCTGCAGCAGCACAACCC  40
   TGCACACCCACCATGGATGTCTTCAAGAAGGGCTTCTCCA  80
   TCGCCAAGGAGGGXGTGGTGGGTGCGGTGGAAAAGACCAA  120
   GCAGGGGGTGACGGAAGCAGCTGAGAAGACCAAGGAGGGG  160
   GTCATGTATGTGGGATTACATTTTTTTTTAAAGAAAGAA   200
              210       220       230       240
   ....|....|....|....|....|....|....|....|
   TAAATTAATTGTGATTAAAGTTG  223
```

Figure 10

```
              10        20        30        40
   ....|....|....|....|....|....|....|....|
   TTTTTTXAGGGGGGGAAAACAGGGAATAXAAAAAXAXGGGG  40
   GGGGGTTTTTXXGGGGGGGGGGGGGAAAAXGGTTXGGGGGX  80
   XAACCXAAAXAAAXXCCXAXGGGGGGGGGXXAXTXAAXTTT  120
   TGGGAACCCAAAGCCCXAGGAGGATTTTTXGTXAAXAACG  160
   TXACCTCXAGTGGGXCGAGGAAGACCAAGGAAAXGCCCAA  200
              210       220       230       240
   ....|....|....|....|....|....|....|....|
   CXCGGTTGAXCGAGGCTGTGGTGAACAXCGTXCAACXCTG  240
   TGCCCXCCAAXAXCGTGGAGGXGGCGGAGAACATCSCGGT  280
   CACCTCCGGGGTGGTGCGCMAGGAGGACTTGAGGCCATCT  320
   KCCCCCCMACAGGAGGGTGTGGCATCCMAAGARAAAGAGG  360
   AAGTGGCAGAGGAGGCCCAGAGTGGGGGARACTAGAGGGC  400
              410       420       430       440
   ....|....|....|....|....|....|....|....|
   TACAGGCCAGCGTGGATGACCTGAAGAGCGCTCCTCTGCC  440
   TTGGACACCATCCCCTCCTAGCACAAGGAGTGCCCGCCTT  480
   GAGTGACATGCGGCTGCCCACGCTCCTGCCCTCGTCTTCC  520
   TGGCCACCCTTGGCCTGTCCACCTGTGCTGCTGCACCAAC  560
   CTCACTGCCCTCCCTCGGCCCCACCCACCCTCTGGTCCTT  600
              610       620       630       640
   ....|....|....|....|....|....|....|....|
   CTGACCCCACTTATGCTGCTGTGAATTTTTTTTTTAAATG  640
   ATTCCAAATAAAACTTGAGCCCACTCCAAAAAAAAAA    677
```

Figure 11 alpha-SYN exons 1-2

```
         10        20        30        40
         |         |         |         |
AATTTCAGCGATGCGAGGGCAAAGCGCTCTCGGCGGTGCG   40
GTGTGAGCCACCTCCCGGCGCTGCCTGTCTCCTCCAGCAG   80
CTCCCCAAGGGATAGGCTCTGCCCTTGGTGGTCGACCCTC  120
AGGCCCTCGNTCTCCCAGGNCGACTCTGACGAGGGGTAGG  160
GGGTGGTCCCCNGGAGGACCCAGAGGAAAGGCNGGGACAA  200
        210       220       230       240
         |         |         |         |
GAAGGGAGGGGAAGGGGAAAGAGGAAGAGGCATCATCCCT  240
AGCCCAACCGCTCCCGATCTCCACAAGAGTGCTCGTGACC  280
CTAAACTTAACGTGAGGCGCAAAAGCGCCCCAACCTTTTC  320
CCGCCTTGNNCCAGGCAGGCGGCTGGAGTTGATGGCTCAC  360
CCCGCGCCCCTGCCCCATCCCCATCCGAGATAGGGACGA   400
        410       420       430       440
         |         |         |         |
GGAGCACGCTGCAGGGAAAGCAGCGAGCGCCGGGAGAGGG  440
GCGGGCAGAAGCGCTGACAAATCAGCGGTGGGGGCGGAGA  480
GCCGAGGAGAAGGAGAAGGAGGAGGACTAGGAGGAGGAGG  520
ACGGCGACGACCAGAAGGGGCCCAAGAGAGGGGGCGAGCG  560
ACCGAGCGCCGCGACGCGAAGTGAGGTGCGTGCGGGCTCA  600
        610       620       630       640
         |         |         |         |
GCGCAGACCCCGGCCCGGCCCCTCCTGAGAGCGTCCTGGG  640
CGCTCCCTCACGCCTTGCCTTCAAGCCTTCTGCCTTTCCA  680
CCCTCGTGAGCGGAGAACTGGGAGTGGCCATTCGACGACA  720
GGTTAGCGGGTTTGCCTCCCACTCCCCCAGCCTCGCGTCG  760
CCGGCTCACAGCGGCCTCCTCTGGGACAGTCCCCCCCGG   800
        810       820       830       840
         |         |         |         |
GTGCCCCTCCGCCCTTCCTGTGCGCTCCTTTTCCTTCTTC  840
TTTCCTATTAAATATTATTTGGGAATTGTTTAAATTTTTT  880
TTTTAAAAAAAGAGAGAGGCGNGGAGGAGTCGGAGTTGTG  920
GAGAAGCAGAGGGACTCAGGTAAGTACCTGTGGATCTAAA  960
CGGGNGTCTTTGGAAATCCTGGAGAACGCCGGATGGAGAC 1000
       1010      1020      1030      1040
         |         |         |         |
GAATGGTCGTGGGNACCGGGAGGGGGTGGTGCTGCCATGA 1040
GGACCGCTGGGCCAGGTCTCTGGGAGGTGAGTACTTGTCC 1080
TTTGGGGAGCCTAAGGAAAGAGACTTGACCTGGCTTTCGT 1120
CCTGCTTCTGATATTCCCTTCTCCACAAGGGCTGAGAGNT 1160
TAGGCTGCTTCTCCGGGATCC                    1181
```

Figure 11 cont.

alpha-SYN exon 3

```
          10        20        30        40
    ....|....|....|....|....|....|....|....|
    CTTAAAAGAGTCTCACACTTTGGAGGGTTTCTCATGATTT  40
    TTCAGTGTTTTTTGTTTATTTTTCCCCGAAAGTTCTCATT  80
    CAAAGTGTATTTTATGTTTTCCAGTGTGGTGTAAAGAAAT 120
    TCATTAGCCATGGATGTATTCATGAAGGACTTTCAAAGG  160
    CCAAGGAGGGAGTTGTGGCTGCTGCTGAGAAAACCAAACA 200
         210       220       230       240
    ....|....|....|....|....|....|....|....|
    GGGTGTGGCAGAAGCAGCAGGAAAGACAAAAGAGGGTGTT 240
    CTCTATGTAGGTAGGTAAACCCCAAATGTCAGTTTGGTGC 280
    TTGTTCATGAGTGATGGGTTAGGATAACAATACTCTAAAT 320
    GCTGGTAGTTCTCTCTCTTGATTCATTTTTGCATCATTGC 360
    TTGTCAAAAAGGTGGACTGAGTCAGAGGTATGTGTAGGTA 400
         410       420       430       440
    ....|....|....|....|....|....|....|....|
    GGTGAATGTGAACGTGTGTATNTGAGCTAATAGTAAAAAT 440
    GCGACTGTTTGCTTTTCAGATTTTTAATTTTGCCTAATAT 480
    NTATGACTTNTTAAAATGAATGTTTCTGTACTACATAATT 520
    CTATNTCAGAGACAGT 536
```

Figure 11 cont.

alpha-SYN exon 4

```
         10        20        30        40
....|....|....|....|....|....|....|....|
CTGCAGGTCAACGGATCTGTCTCTAGTGCTGTACTTTTAA  40
AGCTTCTACAGTTCTGAATTCAAAATTATCTTCTCACTGG  80
GCCCCGGTGTTATCTCATTCTTTTTTCTCCTCTGTAAGTT  120
GACATGTGATGTGGGAACAAAGGGGATAAAGTCATTATTT  160
TGTGCTAAAATCGTAATTGGAGAGGACCTCCTGTTAGCTG  200
        210       220       230       240
....|....|....|....|....|....|....|....|
GGCTTTCTTCTATNTATTGTGGTGGTTAGGAGTTCCTTCT  240
TCTAGTTTTAGGATATATATATATTTTTTCTTTCCCT     280
GAAGATATAATAATATATATACTTCTGAAGATTGAGATTT  320
TTAAATTAGTTGTATTGAAAACTAGCTAATCAGCAATTTA  360
AGGCTAGCTTGAGACTTATGTCTTGAATTTGTTTTTGTAG  400
        410       420       430       440
....|....|....|....|....|....|....|....|
GCTCCAAAACCAAGGAGGGAGTGGTGCATGGTGTGGCAAC  440
AGGTAAGCTCCATTGTGCTTATATCAAAGATGATATNTAA  480
AGTATCTAGTGATTAGTGTGGCCCAGTATCAAGATTCCTA  520
TGAAATTGTAAAACAATCACTGAGCATCTAAGAACATATC  560
AGTCTTATTGAAACTGAATTCTTTATAAAGTATTTTTAAA  600
        610       620       630       640
....|....|....|....|....|....|....|....|
TAGGTAAATATTGATTATAAATAAAAAATATACTTGCCAA  640
GAATAATGAG  650
```

Figure 11 cont.

alpha-SYN exon 5

```
            10        20        30        40
ATATCTTAGCCAAGATTCAATGTTTGGTTGAACCACACTC  40
ACTTGACATCTTGGTGGCTTTTGTTTCTTCTGACCACTCA  80
GTTATCTATGGCATGTGTAGATACAGGTGTATGGAANCGA 120
TGGCTAGTGGAAGTGGAATGATTTTAAGTCACTGTTATTC 160
TACCACCCTTTAATCTGTTGTTGCTCTTTATTTGTACCAG 200
           210       220       230       240
TGGCTGAGAAGACCAAAGAGCAAGTGACAAATGTTGGAGG 240
AGCAGTGGTGACGGGTGTGACAGCAGTAGCCCAGAAGACA 280
GTGGAGGGAGCAGGGAGCATTGCAGCAGCCACTGGCTTTG 320
TCAAAAAGGACCAGTTGGGCAAGGTATGGCTGTGTACGTT 360
TTGTGTTACATTTATAAGCTGGTGAGATTACGGTTCATTT 400
           410       420       430       440
TCATGTGAAGCCTGGAGGCAGGAGCAAGATACTTACTGTG 440
GGGAACGGCTACCTGACCCTCCCCTTGTGAAAAAGTGCTA 480
CCTTTATATTGGTCTTGCTTGTTT 504
```

Figure 11 cont.

alpha-SYN exon 6

```
         10        20        30        40
AAAAGTTTACATACTTTGAGGTTGATAACCCATGTTGCCG  40
CAATGTTTCCCCGGAGGCATTGTGGAGTTTAGAATGCCAG  80
TAGTAATATTAAGGTGTGCCATTTTCAAGATCCGTGGCCA  120
ACATCCCTATATGTAAGATTTTTCCAAAACATGGTTCTGA  160
TTTTTAAAAGTGAAAAATGCTACTTCATCATGTTCTTTTT  200
         210       220       230       240
GTGCTTCTTACTTTAAATATTAGAATGAAGAAGGAGCCCC  240
ACAGGAAGGAATTCTGGAAGATATGCCTGTGGATCCTGAC  280
AATGAGGCTTATGAAATGCCTTCTGAGGTAGGAGTCCAAG  320
CTGAATCTTTCTAACAAGACAGTACCAAAAACCTGTCATT  360
GTCACATTTCTCTTTCATTAGTGCTTAGTGAGAATCATTT  400
         410       420       430       440
GCTCTCTACATGCTCATTACGTGGACAACTTGCAAGTTAA  440
GAATAGTTTTTACATTTTTAAAGGGTCCTTAAAAAAAAAG  480
AGGAGGAGGAAGATGAAGAAGAGGAAGAAAGGATGTAAAA  520
GAAATCATATGTAGTCCACATAGCTTAATATACNTACTAC  560
TTGACCCTTTACAGGAAAAGCTTTACTAACCCCTGCATTA  600
         610       620       630       640
GAGAATATATTTTTTTGCAAAAACATTGATTGTAAATTTT  640
AGTGTAAAGTGGGGAGCCATTTCCTATCTCATTGGCTGTC  680
CAGTGCTGATGCGTAATTGAAACTTATACTAACAGTGTGT  720
GCTGTCT  727
```

Figure 11 cont.

alpha-SYN exon 7

```
         10        20        30        40
TTTTGATTTTTCTAATATTAGGAAGGGTATCAAGACTACG  40
AACCTGAAGCCTAAGAAATATCTTTGCTCCCAGTTTCTTG  80
AGATCTGCTGACAGATGTTCCATCCTGTACAAGTGCTCAG 120
TTCCAATGTGCCCAGTCATGACATTTCTCAAAGTTTTTAC 160
AGTGTATCTCGAAGTCTTCCATCAGCAGTGATTGAAGCAT 200
        210       220       230       240
CTGTACCTGCCCCCACTCAGCATTTCGGTGCTTCCCTTTC 240
ACTGAAGTGAATACATGGTAGCAGGGTCTTTGTGTGCTGT 280
GGATTTTGTGGCTTCAATCTACGATGTTAAAACAAATTAA 320
AAACACCTAAGTGACTACCACTTATTTCTAAATCCTCACT 360
ATTTTTTGTTGCTGTTGTTCAGAAGTTGTTAGTGATTTG  400
        410       420       430       440
CTATCATATATTATNAGATTTTTAGGTGTCTTTTAATGAT 440
ACTGTCTAAGAATAATGACGTATTGTGAAATTTGTTAATA 480
TATATNATACTTAAAAATATGTGAGCATGAAACTATGCAC 520
CTATAATACTAAATATGAAATTTTACCATTTTGCGATGTG 560
TTTTATTCACTTGTGTTTGTATATNAATGGTGAGAATTAA 600
        610       620       630       640
AATAAAACGTTATCTCATTGCAAAAATATTTTATTTTTAT 640
CCCATCTCACTTTAATAATAAAAATCATGCTTATAAGCAA 680
CATGAATTAAGAACTGACACAAAGGACAAAAATATAAAGT 720
TATTAATAGCCATTTGAAGAAGGAGGAATTTTAGAAGAGG 760
TAGAGAAAATGGAACATTAACCCTACACTCGGAATTCCCT 800
        810       820       830       840
GAAGCAACACTGCCAGAAGTGTGTTTGGTATGCACTGGT  840
TCCTTAAGTGGCTGTGATTAATTATTGAAAGTGGGGTGTT 880
GAAGACCCCAACTACTATTGTAGAGTGGTCTATTTCTCCC 920
TTCAATCCTGTCAATGTTTGCTTTACGTATTTTGGGGAAC 960
TGTTGTTTGATGTGTATGTGTTTATAATTGTTATACATTT 1000
       1010      1020      1030      1040
TTAATTGAGCCTTTTATTAACATATATTGTTATTTTTGTC 1040
TCGAAATAATTTTTTAGTTAAAATCTATTTTGTCTGATAT 1080
TGGTGTGAATGCTGTACCTTTCTGACAATAAATAATATNC 1120
GACCATGAATAAAAAAAAAAAAAAAGTGGGTTCCCGGGAA 1160
CTAAGCAGTGTAGAAGATGATTTTGACTACACCCTCCTTA 1200
```

Figure 11 cont.

alpha-SYN exon 7

```
           1210      1220      1230      1240
GAGAGCCATAAGACACATTAGCACATATTAGCACATTCAA 1240
GGCTCTGAGAGAATGTGGTTAACTTTGTTTAACTCAGCAT 1280
TCCTCACTTTTTTTTTTAATCATCAGAAATTCTCTCTCT  1320
CTCTCTCTTTTTCTCTCGCTCTCTTTTTTTTTTTTTTTT  1360
TTTACAGGAAATGCCTTTAAACATCGTTGGGAACTACCA  1400
           1410      1420      1430      1440
GAGTCACCTTAAAGGGAGNATCAATTCTCTAGGACTGGAT 1440
AAAAATTTCATGGGCCTCCTTTAAAATGTTGCCCAAATAT 1480
ATGGAATTCTAGGGGTTTTTCCNTAGGGGGAAGGGTTTTT 1520
TCTCTTTTCNGGGGAGGATCCTTTTAACNCCCCNGGGGGG 1560
NGCCCGGAAAATAAACTTGGNGGGGGGGNAAAACTT     1596
```

CLONING OF A GENE MUTATION FOR PARKINSON'S DISEASE

This application is based on provisional application No. 60/050,684 filed Jun. 25, 1997 which is relied upon and hereby expressly incorporated by reference herein.

BACKGROUND OF THE INVENTION

1. Field of the Invention

Parkinson's disease (PD) is a common neurodegenerative disorder with a lifetime incidence of approximately 2 percent. A pattern of familial aggregation has been documented for the disorder, and it was recently reported that a PD susceptibility gene in a large Italian kindred is located on the long arm of human chromosome 4. We have identified a mutation in the alpha synuclein gene, which codes for a presynaptic protein thought to be involved in neuronal plasticity, in the Italian kindred and in three unrelated families of Greek origin with autosomal dominant inheritance for the PD phenotype. This finding of a specific molecular alteration which is causative for PD will permit the detailed understanding of the pathophysiology of the disorder. In addition, methods of screening nucleic acids for the presence of mutations in the synuclein gene to test for predisposition to Parkinson's Disease are now possible.

2. Technology Background

Parkinson's disease (PD) was first described by James Parkinson in 1817 (1). The clinical manifestations of this neurodegenerative disorder include resting tremor, muscular rigidity, bradykinesia and postural instability. A relatively specific pathological feature accompanying the neuronal degeneration is the intracytoplasmic inclusion body, known as the Lewy body, which is found in many regions including the substantia nigra, locus ceruleus, nucleus basalis, hypothalamus, cerebral cortex, cranial nerve motor nuclei, and the central and peripheral divisions of the autonomic nervous system (1).

In many cases a heritable factor predisposes to the development of the clinical syndrome (2). We have recently shown that genetic markers on human chromosome 4q21–q23 segregate with the PD phenotype in a large family of Italian descent (3). The clinical picture of the PD phenotype in the Italian kindred has been well documented to be typical for PD, including Lewy bodies, with the exception of a relatively earlier age of onset of illness at 46±13 years. In this family the penetrance of the gene has been estimated to be 85%, suggesting that a single gene defect is sufficient to determine the PD phenotype.

We now report the identification of a mutation in the alpha synuclein gene that is associated with Parkinson's disease. The mutation, an Ala53Thr substitution, was found to be linked to the PD phenotype in four independent PD families and absent from 314 control chromosomes, providing strong genetic evidence that this mutation in the human alpha synuclein gene is causative for the PD phenotype in these families.

The Ala53Thr substitution is localized in a region of the protein whose secondary structure predicts an alpha helical formation, bounded by beta sheets. Substitution of the alanine with threonine is predicted to disrupt the alpha helix and extend the beta sheet structure. Beta pleated sheets are thought to be involved in the self aggregation of proteins which could lead to the formation of amyloid like structures (6).

This was already tested in the case of NAC35, the 35 amino acid peptide derived from alpha-synuclein that was first isolated from plaques found in patients with Alzheimer's disease (4). NAC35 was shown to self aggregate and form amyloid fibril which shared the 'amyloid' characteristics of insolubility in aqueous solutions and green birefringence under polarized light, subsequent to Congo red staining (6). NAC35 is located in the middle of the alpha synuclein molecule and extends from amino acid 61 to amino acid 95. Residue 53, which is found to be mutated in PD, is outside the NAC35 peptide found in amyloid plaques. However, the true size of the NAC peptide involved in the plaques is not known since the protease used to isolate the peptide from AD tissue cuts at lysine 60 of the alpha synuclein protein. It is therefore possible that amino acid 53 may be part of the NAC peptide found in plaques. In crosslinking experiments with beta amyloid (Abeta), it was demonstrated (6) that residues 1–56 and 57–97 specifically bind amyloid and that a synthetic peptide consisting of residues 32–57 performed similarly.

Three members of the synuclein family have been characterized in the rat, with SYN1 exhibiting 95% homology with the human alpha-synuclein protein (7). SYN 1 of the rat is expressed in many regions of the brain, with high levels found in the olfactory bulb and tract, the hippocampus, dentate gyrus, habenula, amygdala and piriform cortex, and with intermediate levels in the granular layer of the cerebellum, substantia nigra, caudate-putamen, and dorsal raphe (7). This pattern of expression coincides with the distribution of the Lewy bodies found in brains of patients with Parkinson's disease. It is also interesting to note that decrease in olfactory sense often accompanies the syndromic features of Parkinson's disease, and in many cases it is proposed that hyposmia is a prodromic sign of the illness (8).

In the zebra-finch the homologue to alpha synuclein, synelfin, is thought to be involved in the process of song learning, suggesting a role for synuclein perhaps in memory and learning (9). In contrast to humans, rats have a threonine at residue 53 of their homologues to the human alpha synuclein gene (FIG. 4). Similarly, the zebra-finch synelfin carries a threonine at amino acid 53, whereas both *Bos taurus* and Torpedo californica do not (10). There are no reports that suggest the presence of Lewy bodies in the brains of the rat or the zebra finch or a phenotype resembling that of PD. Lack of any phenotype could be explained by a combination of factors, including the following: the relative short life span of rodents may prohibit the observation of a late onset disorder, interaction with other cellular components not present in the rat may be required for the phenotype, absence of a critical environmental trigger in the rodents, or finally a heterozygous status Ala/Thr may be necessary for the production of a phenotype.

Studies of early onset AD have previously documented that missense mutations can cause an adult onset neurodegenerative disorder. Of the 31 mutations described so far in the loci for presenilin 1 and 2, thirty were missense and one was a splice variant (11). Missense mutations in the prion protein have also been implicated in the amyloid production seen in Gerstmann-Straussler-Scheinker and Creutzfeld-Jakob diseases, both forms of spongiform encephalopathy (12). Studies in these neurodegenerative disorders have pointed to the importance of the physical chemical properties of mutant cellular proteins in initiating and propagating neuronal lesions leading to disease. Similar studies in the synuclein protein family may provide valuable insights into the etiology and pathogenesis of PD.

Similarly with the mutations in the presenilin genes in patients with early onset Alzheimer's disease, the mutation identified in the alpha synuclein gene is unlikely to account for the majority of sporadic and familial cases of PD. However, this mutation may account for a significant proportion of those families with a highly penetrant, early onset autosomal dominant PD phenotype.

All publications and patent applications herein are incorporated by reference to the same extent as if each individual publication or patent application was specifically and individually indicated to be incorporated by reference.

SUMMARY OF THE INVENTION

As described herein, we have discovered that particular mutations in the alpha synuclein gene are associated with predisposition to Parkinson's disease. Accordingly, the present invention includes an isolated nucleic acid comprising a mutated synuclein gene. In particular, the isolated nucleic acid of the present invention contains at least one mutation in the alpha synuclein gene at base pair position 209 of Genbank # L08850, which, in particular, is a change from guanine to adenine. However, since other mutations in the alpha synuclein gene may also lead to Parkinson's Disease (PD), other mutations are also included. In addition, it is conceivable that mutations is in the related beta (46) (SEQ ID NO: 11) and gamma (SEQ ID NOS: 12 and 13) may also lead to PD. Thus, mutated homologues of the alpha synuclein gene are also included in the present invention. Vectors comprising the isolated nucleic acid and host cells comprising such vectors are included as well.

Knowledge of particular genes that are associated with PD allows for the search for other specific PD mutations. Accordingly, the present invention also includes a method of using a synuclein gene sequence to identify specific PD mutations. Such mutations may occur in an unrelated population or in a family that demonstrates passage of PD within the family tree.

Since knowledge of mutations associated with Parkinson's disease allows the development of genetic screens that test for an individual's chances of being predisposed to the disease, and such tests may be performed by hybridization analysis using oligonucleotides complementary to the sequence of interest or by PCR amplification using oligonucleotides that are complementary to sequences flanking the mutation, the present invention also includes oligonucleotides complementary to a portion of the synuclein gene, wherein said portion comprises or flanks a mutation associated with predisposition to Parkinson's Disease. In particular, the oligonucleotides of the present invention will have a sequence that is complementary to a sequence from the alpha synuclein gene that includes or flanks base pair position 209. And in particular, this mutation is a change from guanine to adenine at this position.

Vectors comprising an isolated nucleic acid encoding a mutated synuclein gene will allow the production and isolation of the mutant protein in an appropriate host cell using techniques well known in the art. Alternatively, peptides may be chemically synthesized using techniques also well known in the art. Isolation of such a protein or peptides thereof will allow the study of the molecular mechanisms which lead to development of Parkinson's disease. Accordingly, the present invention also includes an isolated synuclein protein or peptide containing at least one mutation. In particular, this mutation is at a position corresponding to the fifty-third amino acid in the native alpha synuclein protein, and in particular, this mutation is an alanine to threonine substitution.

Peptides corresponding to portions or the entirety of a synuclein gene may be useful as drugs for inhibiting the self-aggregation of mutant proteins that is thought to lead to Parkinson's disease. Accordingly, the present invention includes a method of testing peptides and other compounds for the ability to interfere with this self-aggregation. Self-aggregation can be tested using a number of established methods, including Congo red staining, electron microscopy pictures of amyloid fibrils, and circular dichroism (CD) spectrophotometry. Using a peptide derived from the alpha synuclein protein that includes the mutant THR amino acid at position 53 alone or in combination with a normal peptide may allow testing for drugs that can inhibit the aggregation or dissolve an aggregate. This procedure can be used to rapidly identify agents that could be used in animal studies, clinical trials, or as diagnostic tools.

Possession of isolated synuclein proteins or peptides will also allow the isolation of specific antibodies using techniques well known in the art. Such antibodies may distinguish a mutant synuclein protein from its wildtype counterpart, and therefor could also be used in diagnostic screens. Alternatively, such antibodies may also be used to inhibit the self-aggregation of proteins during the progression of Parkinson's disease. Accordingly, the present invention also includes antibodies specific for a mutated synuclein protein or peptide. It should be understood that useful derivatives of such antibodies, such as Fv fragments and Fab fragments, are also included.

The above aspects of the present invention will allow methods of detecting subjects at increased risk for Parkinson's Disease. Such a method comprises obtaining a sample comprising nucleic acids from the subjects, and detecting in the nucleic acids the presence of a mutation which is associated with Parkinson's disease. In particular, the mutation detected by the method of the present invention is located on human chromosome four, preferably in the alpha synuclein gene. In particular, the mutation causes an amino acid substitution at position 53 of the alpha synuclein gene, which is, in particular, an alanine to threonine substitution.

The detecting step of the method of the present invention may be accomplished several different ways as will be described in further depth below. All such methods are well known to those of ordinary skill in the art.

For instance, said detecting step may comprise combining a nucleotide probe which selectively hybridizes to a nucleic acid containing a mutation associated with a predisposition to Parkinson's disease, and detecting the presence of hybridization. Such a probe may be an oligonucleotide that is complementary to a portion of the synuclein gene, wherein said portion comprises the mutation. In particular, such an oligonucleotide is complementary to a mutated alpha synuclein gene having at least one mutation at base pair position 209. In particular, this mutation is a change from guanine to adenine.

The detecting step of the method of the present invention may also comprise amplifying a nucleic acid product comprising said mutation, and detecting the presence of said mutation in the amplified product using any nucleic acid sequencing procedure known in the art. Alternatively, the detecting step may comprise selectively amplifying a nucleic acid product comprising said mutation, and detecting the presence of amplification using any appropriate method known in the art. Such methods include gel electrophoresis of amplified nucleic acids, and detection of radiolabeled amplified nucleic acids using autoradiographic film or any other detection method known in the art.

The amplifying step of the present invention may be performed using the polymerase chain reaction (PCR), reverse transcriptase PCR (RTPCR), or any other type of PCR reaction known in the art. Accordingly, such a step will comprise at least one annealing step whereby at least one oligonucleotide is annealed to said sample of nucleic acids. In particular, said amplifying step uses two oligonucleotides. And in particular, the two oligonucleotides have the sequences given in SEQ ID NOS: 2 and 3.

Alternatively, the detecting step of the method of the present invention comprises detecting the presence or absence of a restriction endonuclease site as detected by enzymatic digest of a nucleic acid sample. Such a detecting means will be possible when a mutation associated with a predisposition to Parkinson's disease results in a sequence having a new restriction endonuclease cleavage site, or loss of a native restriction endonuclease site. In particular, the mutation associated with Parkinson's disease results in the formation of a non-native Tsp45I restriction endonuclease site.

Alternatively, the detecting step of the present invention may be performed using a gene-specific primer and subsequent chain termination at the position of the mutation using DNA polymerase and labeled nucleotides or dideoxynucleotides. The presence of nucleic acids in which a dideoxynucleotide corresponding to the mutation of interest is incorporated at the appropriate position may be detected by any means known in the art, including detection of radiolabeled dideoxynucleotides using, for example, autoradiographic film, or detection of fluorescently-labeled dideoxynucleotides.

Since the methods and compounds of the present invention will be useful in diagnostic screening procedures aimed at identifying individuals having a predisposition for Parkinson's disease, the present invention also includes diagnostic kits which include the compounds of the present invention in a form that allows such compounds to be used quickly and easily for the designated purpose.

Finally, the inventors also contemplate that the isolated nucleic acid, oligonucleotides and antibodies of the present invention may eventually be used in methods directed at the correction or suppression of Parkinson's disease. For example, oligonucleotides or expression vectors designed from the synuclein nucleic acid sequences of the present invention may one day be used in antisense therapy directed at inhibiting expression of the mutated synuclein protein in patients with Parkinson's disease, or in individuals having a predisposition for Parkinson's disease. Similarly, antibodies specific for the mutated synuclein protein may be useful in therapies directed at inhibiting the self-aggregation of mutated proteins or peptides in patients having Parkinson's disease. Knowledge of gene(s) associated with the development of Parkinson's disease may also allow the design of transgenic animals which express the mutant gene(s). Such animals may serve as a useful disease model, allowing one to test the effects of candidate therapies and therapeutic compositions in the treatment or inhibition of Parkinson's disease.

A detailed description of the present invention is now provided, and should not be considered as limiting on the present invention as described above.

Figure 1:
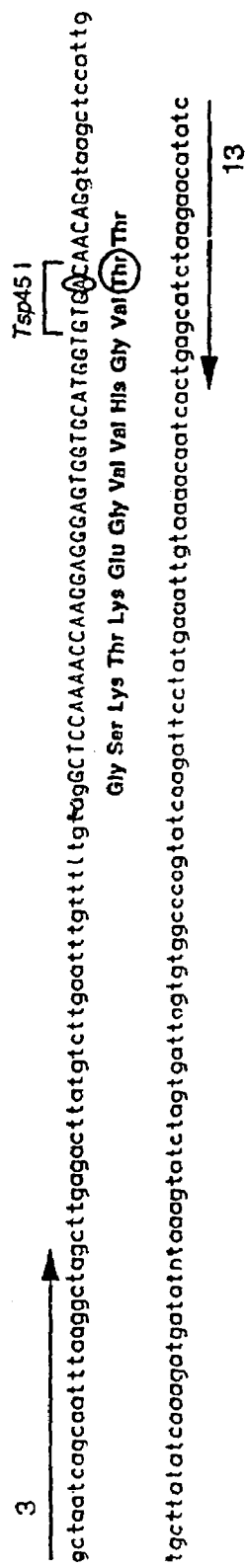
FIG. 1.

DNA sequence of the PCR product used for mutation detection (SEQ ID NO: 1) Oligonucleotide primers are shown by arrows and the numerals 3 and 13 (SEQ ID NOS:2 and 3). Intron sequence is shown in lower case and exon sequence in upper case. Amino acid translation of the exon is shown below the DNA sequence (SEQ ID NO:25). The circled base represents the G209A change in the mutant allele. The resulting amino acid Ala53Thr change is represented by the circled amino acid. The newly created Tsp45 I site is indicated above the DNA sequence.

FIG. 2.

Mutation analysis of the G209A change is shown in a subpedigree of the Italian kindred. Filled symbols represent affected individuals. Numerical identifiers, denote the individuals immediately above. Tsp45 I digestion of PCR products is shown at the bottom of the figure, and fragment sizes are indicated on the right in base pairs.

FIG. 3.

Mutation analysis of the G209A change in RT PCR products (7). Lane 1: 100 bp ladder, lanes 2 and 3 normal control, lanes 4 and 5 PD patient, lane 6 negative control without RT enzyme. Sizes are indicated on the right in base pairs. Lanes 2 and 4 show uncut DNA and lanes 3 and 5 show DNA cut with Tsp45 I.

FIG. 4.

Sequence alignments of alpha synuclein homologues in different species. Accession numbers for the sequences used were as follows: *Homo sapiens* Swiss-Prot P37377 (SEQ ID NO:5), *Bos taurus* Swiss-Prot P33567 (SEQ ID NO:6), Serinus canaria genbanc L33860 (SEQ ID NO:7), Torpedo californica Swiss-Prot P37379 (SEQ ID NO:8). Numbering on top of the alignments is according to the human sequence. Amino acid 53, which is the site of the Ala53Thr change, is circled.

FIG. 5.

The pedigree of a large family with PD (3). The clinical and pathological features of some members of this kindred were previously reported.

FIG. 6.

Multipoint LOD score analysis between chromosome 4q markers and the PD locus.

FIG. 7.

A table of human synuclein clones identified from various databases. Columns labeled 5' and 3' show the sequence acquisition numbers. Clones were identified by homology to protein or nucleic acid sequence. Human gamma clones were identified by homology to known mouse and rat gamma synuclein sequences.

FIG. 8.

Sequence of BAC clone 139A20 for human beta synuclein. BAC clone was isolated using primers to known database sequences described in FIG. 7. The sequence shown includes all coding exon sequences and some non-coding intronic sequences. (SEQ ID NO:11)

FIG. 9.

Sequence from the 5' end of BAC clone 174P13 for human gamma synuclein. The BAC clone was isolated with primers from the database sequences described in FIG. 7. (SEQ ID NO:12)

FIG. 10.

Sequence from the 3' end of BAC clone 174P13 for human gamma synuclein. BAC clone was isolated as described in FIG. 9. The entire human gamma synuclein gene has now been sequenced and has been deposited in GenBank: accession number AF044311. (SEQ ID NO: 13)

FIG. 11.

Sequence of exons 1–7 of the human alpha synuclein gene, plus some flanking intronic sequence for each exon (SEQ ID NOS: 14–19). Exons 1–2 are SEQ ID NO: 14, exon 3 is SEQ ID NO: 15, exon 4 is SEQ ID NO: 16, exon 5 is SEQ ID NO: 17, exon 6 is SEQ ID NO:18 and exon 7 is SEQ ID NO:19.

DETAILED DESCRIPTION OF THE INVENTION

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For purposes of the present invention, the following terms are defined below.

This invention provides a method of diagnosing or predicting a predisposition to Parkinson's disease. The method comprises detecting in a sample from a subject the presence of a mutation, for example, in nucleotide position 209 of the human alpha synuclein gene. The presence of the mutation indicates the presence of or a predisposition to Parkinson's disease.

As used herein, the term "gene" primarily relates to a coding sequence, but can also include some or all of the surrounding or flanking regulatory regions or introns. The term "gene" specifically includes artificial or recombinant genes created from cDNA or genomic DNA, including recombinant genes based upon splice variants.

As used herein, the term "synuclein" gene or protein may refer to the alpha synuclein gene or any homologue thereof. A "homologue" is understood to mean any related gene or protein that is at least 25% homologous to the alpha synuclein gene or protein or performs a related function. Preferably, a synuclein gene or protein refers to alpha, beta or gamma synuclein, but most preferably refers to alpha synuclein.

As used herein, an "isolated nucleic acid" is a ribonucleic acid, deoxyribonucleic acid, or nucleic acid analog comprising a polynucleotide sequence that has been isolated or separated from sequences that are immediately contiguous, i.e. on the 5' and 3' ends, in the naturally occurring genome of the organism from which it is derived. The term therefor includes, for example, a recombinant nucleic acid which is incorporated into a vector, into an autonomously replicating plasmid or virus, or into the genomic DNA of a prokaryote or eukaryote, or which exists as a separate molecule independent from any other sequences.

An isolated nucleic acid of the present invention may be "operatively linked" to an expression control sequence or regulatory region. As used herein, "operatively linked" means that the components are joined in such a way that the expression, transcription or translation of the sequence is under the influence or control of the regulatory region.

As used herein, a "predisposition" to Parkinson's disease means an increased probability of developing Parkinson's disease during the subject's lifetime as compared to the average individual.

Pertaining to this probability, a LOD score is a measure of genetic linkage used herein, defined as the log ratio of the probability that the data would have arisen if the loci are linked to the probability that the data could have arisen from unlinked loci. The conventional threshold for declaring linkage is a LOD score of 3.0, that is, a 1000:1 ratio (which must be compared with the 50:1 probability that any random pair of loci will be unlinked).

As used herein, reference to "base pair position" or "amino acid position" when referring to an isolated nucleic acid, probe, protein or peptide always indicates the relative position in the native gene or protein.

A "probe" refers to a nucleic acid which has sufficient nucleotides surrounding the codons at the mutation positions to distinguish the nucleic acid from nucleic acids encoding non-related genes. The specific length of the nucleic acid is a matter of routine choice based on the desired function of the sequence. For example, if one is making probes to detect the mutation in base pair position 209, the length of the nucleic acid is preferably small, but must be long enough to prevent hybridization to undesired background sequences. However, if the desired hybridization is to a nucleic acid which has been amplified, background hybridization is less of a concern and a smaller probe can be used. In general, such a probe will be between 10 and 100 nucleotides, especially between 10 and 40 and preferably between 15 and 25 nucleotides in length. It is apparent to one of skill in the art that nucleotide substitutions, deletions, and additions may be incorporated into the polynucleotides of the invention. However, such nucleotide substitutions, deletions, and additions should not substantially disrupt the ability of the polynucleotide to hybridize under conditions that are sufficiently stringent to result in specific hybridization.

As used herein with respect to genes, "the term "normal" refers to a gene which encodes a normal protein. As used herein with respect to proteins, the term "normal" means a protein which performs its usual or normal physiological role and which is not associated with, or causative of, a pathogenic condition or state. Therefor, the term "normal" is generally synonomous with the phrase "wild type".

For any given gene or corresponding protein, a multiplicity of normal allelic variants may exist, none of which is associated with the development of a pathogenic condition or disease state. Such normal allelic variants include, but are not limited to, variants in which one or more nucleotide substitutions do not result in a change in the encoded amino acid sequence.

As used herein, the term "mutation" generally refers to a mutation in a gene that is associated with a predisposition to Parkinson's disease. "Mutant" can specifically refer to a mutation at nucleotide position 209 of the synuclein gene, and is in particularly a G to A transition. However, other mutations in the synuclein gene or other genes which are associated with a predisposition to Parkinson's disease are also encompassed. Furthermore, the term "mutation" is not limited to transition mutations, but can also mean a deletion, insertion or transversion as well.

The term "mutant", as it applies to synuclein genes, is not intended to embrace sequence variants which, due to the degeneracy of the genetic code, encode proteins identical to the normal sequences disclosed or otherwise enabled herein; nor is it intended to embrace sequence variants which, although they encode different proteins, encode proteins which are functionally equivalent to normal synuclein proteins. The term "mutant" means a protein which does not perform its usual or normal physiological role and which is associated with, or causative of, a pathogenic condition or state.

Since a mutation can be a substitution, deletion or insertion, a mutated synuclein "protein" is understood to refer to the amino acid sequence resulting from any such mutation whether the resulting protein is shorter, longer or modified, i.e. due to an alteration in reading frame or generation of stop codon. In addition, "peptide" is understood to refer to a portion of the mutated protein that is preferably at least five base pairs long, and more preferably at least 10 base pairs long. This portion may be derived from the amino or carboxyl terminus, or it may be an internal portion of the full length protein. As such, a peptide may be chemically synthesized using any method known in the art, or may be made using a recombinant DNA technology and an appropriate purification scheme or isolated from the native protein using enzymatic digestion.

As used herein, the term "substantially pure" means a preparation which is at least 60% by weight the compound of interest. Preferably the preparation is at least 75, more preferably 90%, and most preferably at least 99%, by weight the compound of interest. Purity can be measured by any appropriate method, i.e. column chromatography, gel electrophoresis or HPLC analysis.

"Specific or selective hybridization" as used herein means the formation of hybrids between a probe nucleic acid (e.g., a nucleic acid which may include substitutions, deletions, and/or additions) and a specific target nucleic acid (e.g., a nucleic acid having the mutated sequence), wherein the probe preferentially hybridizes to the specific target such that, for example, a band corresponding to the mutated DNA or restriction fragment thereof can be identified on a Southern blot, whereas a corresponding normal or wild-type DNA is not identified or can be discriminated from a variant DNA on the basis of signal intensity. Hybridization probes capable of specific hybridization to detect a single-base mismatch may be designed according to methods known in the art (13–17).

"Stringent" as it refers to hybridization conditions is a term of art understood by those of ordinary skill to refer to those conditions of temperature, chaotrophic acids, buffer and ionic strength which permit hybridization of a particular nucleic acid sequence to its complementary sequence and not to substantially different sequences. The exact conditions which constitute "stringent" conditions depend on the nature of the nucleic acid sequence, the length of the sequence, and the frequency of occurrence of subsets of that sequence within other non-identical sequences. By varying hybridization conditions from a level of stringency at which non-specific hybridization occurs to a level at which only specific hybridization occurs, one of ordinary skill in the art can, without undue experimentation, determine conditions which will allow a given sequence to hybridize only with complementary sequences.

Suitable ranges of stringency conditions are described in Sambrook et al. (13). Hybridization conditions, depending on the length and commonality of a sequence, may include temperatures of 20° C.–65° C. and ionic strengths from 5× to 0.1×SSC. Highly stringent hybridization conditions may include temperatures as low as 40° C.–42° C. (when denaturants such as formamide are included) or up to 60° C.–65° C. in ionic strengths as low as 0.1×SSC. These ranges are, however, only illustrative and, depending on the nature of the target sequence, and possible future technological developments, may be more stringent than necessary. Appropriate conditions may be determined for each specific nucleic acid sequence or oligonucleotide probe using standard control and a level of experimentation that is not considered to be undue by those of skill in the art.

As discussed below in greater detail, the mutation can be detected by many methods. For example, the detecting step can comprise combining a nucleotide probe capable of selectively hybridizing to a nucleic acid containing the mutation with a nucleic acid in the sample and detecting the presence of hybridization. Additionally, the detecting step can comprise amplifying the nucleotides surrounding and including the mutation and detecting the presence of the mutation in the amplified product, or selectively amplifying the nucleotides of the mutation and detecting the presence of amplification. Finally, the detecting step can comprise detecting the presence or absence of a restriction fragment created by an enzyme digest of the sample nucleic acid, or any other detection means known in the art.

Detection Techniques

Once the location of a PD-relevant mutation is known, the methods to detect such a mutation are standard in the art. The sequence of various nucleotide probes can be determined from the known sequence of the relevant gene, especially the sequences surrounding the mutation.

Detection of point mutations using direct probing involves the use of oligonucleotide probes which may be prepared, for example, synthetically or by nick translation. The probes may be suitably labeled using, for example, a radio label, enzyme label, fluorescent label, biotin-avidin label and the like for subsequent visualization by any appropriate assay, i.e. Southern blot hybridization. In this procedure, the labeled probe is reacted with sample DNA that is bound, for example, to a nylon filter under conditions such that only fully complementary sequences hybridize. The areas that carry DNA sequences complementary to the labeled DNA probe become labeled themselves as a consequence of the reannealing reaction. The areas of the filter that exhibit such labeling may then be visualized, for example, by autoradiography.

Methods of manipulating hybridization conditions to achieve varying degrees of specificity are well known in the art. For example, tetra-alkyl ammonium salts may be used to bind selectively to A-T base pairs, thus displacing the dissociation equilibrium and raising the melting temperature. At 3M Me 4NCl, this is sufficient to shift the melting temperature to that of G-C pairs. This results in a marked sharpening of the melting profile. The stringency of hybridization in such an experiment is usually 5_C below the Ti (the irreversible melting temperature of the hybrid formed between the probe and its target sequence) for the given chain length. For a 20mer oligonucleotide probe, the recommended hybridization temperature is about 58_C. The washing temperatures are unique to the sequence under investigation and need to be optimized for each variant.

There are certainly other ways known in the art for adjusting hybridization conditions in view of desired specificity. For instance, although hybridization may be carried out in accordance with conventional hybridization methods under suitable conditions with respect to e.g. stringency, incubation time, temperature, etc, the choice of conditions will depend on the desired degree of complementarity between the fragments to be hybridized. A high degree of complementarity requires more stringent conditions such as low salt concentrations, low ionic strength of the buffer and higher temperatures, whereas a low degree of complementarity requires less stringent conditions, e.g. higher salt concentration, higher ionic strength of the buffer or lower temperatures, for the hybridization to take place.

The support to which DNA or RNA fragments of the sample to be analyzed are bound in denatured form is preferably a solid support and may have any convenient shape. Thus, it may, for instance, be in the form of a plate, e.g. a thin layer or a microtiter plate, a strip, a solid particle e.g. in the form of a bead such as a latex bead, a filter, a film or paper. The solid support may be composed of a polymer, preferably nylon or nitrocellulose.

Alternative probing techniques, such as ligase chain reaction (LCR), may involve the use of mismatch probes, i.e., probes which are fully complementary with the target except at the point of the mutation. The target sequence is then allowed to hybridize both with oligonucleotides which are fully complementary and have oligonucleotides containing a mismatch, under conditions which will distinguish between the two. By manipulating the reaction conditions according to the above considerations, it is possible to obtain hybridization only where there is full complementarity. If a mismatch is present there is significantly reduced hybridization.

The polymerase chain reaction (PCR) is a technique that amplifies specific DNA sequences with remarkable efficiency. Repeated cycles of denaturation, primer annealing and extension carried out with Taq polymerase, e.g., a heat stable DNA polymerase, leads to exponential increases in the concentration of desired DNA sequences. Given a knowledge of the nucleotide sequence of the mutations, synthetic oligonucleotides can be prepared which are complementary to sequences which flank the DNA of interest. Each oligonucleotide is complementary to one of the two strands. The DNA is denatured at high temperatures (e.g., 95_C) and then reannealed in the presence of a large molar excess of oligonucleotides. The oligonucleotides, oriented with their 3' ends pointing towards each other, hybridize to opposite strands of the target sequence and prime enzymatic extension along the nucleic acid template in the presence of the four deoxyribonucleotide triphosphates. The end product is then denatured again for another cycle. After this three-step cycle has been repeated several times, amplification of a DNA segment by more than one million-fold can be achieved. The resulting DNA may then be directly sequenced in order to locate any genetic alteration. Alternatively, it may be possible to prepare oligonucleotides that will only bind to altered DNA, so that PCR will only result in multiplication of the DNA if the mutation is present. Following PCR, direct visualization or allele-specific oligonucleotide hybridization (18) may be used to detect the Parkinson's disease point mutation. Alternatively, PCR may be followed by restriction endonuclease digestion with subsequent analysis of the resultant products.

As shown in the examples, the substitution of G for A at base pair 209 of the synuclein, results in the gain of a Tsp45I site. The gain of this restriction endonuclease recognition site facilitates the detection of the Parkinson's disease mutation using restriction fragment length polymorphism (RFLP) analysis or by detection of the presence or absence of the restriction site in a PCR product that spans base pair position 209.

For RFLP analysis, DNA is obtained, for example from the blood cells of the subject suspected of having Parkinson's disease and from a normal subject, is digested with a restriction endonuclease, and subsequently separated on the basis of size by agarose gel electrophoresis. The Southern technique can then be used to detect, by hybridization with labeled probes, the products of endonuclease digestion. The patterns obtained from the Southern blot can then be compared. Using such an approach, an additional restriction endonuclease site, such as a Tsp45I site, is detected by determining the number of bands detected and comparing this number to the normal subject.

The creation of a new restriction site as a result of a nucleotide substitution at a disclosed mutation site can be readily determined by reference to the genetic code and a list of nucleotide sequences recognized by restriction endonucleases (19).

In general, primers for PCR are usually about 20 bp in length, and are most preferably 15–25 bp. Denaturation of strands usually takes place at 94° C. and extension from the primers is usually at 72° C. The annealing temperature varies according to the sequence under investigation. Examples of reaction times are: 20 mins denaturing; 35 cycles of 2 min, 1 min, 1 min for annealing, extension and denaturation; and finally a 5 min extension step.

PCR "amplification of specific alleles" (PASA) may also be used to detect the presence of the PD mutation. PASA is a rapid method of detecting single-base mutations or polymorphisms (22–28). PASA (also known as allele specific amplification) involves amplification with two oligonucleotide primers such that one is allele-specific. The desired allele is efficiently amplified, while the other allele(s) is poorly amplified because it mismatches with a base at or near the 3' end of the allele-specific primer. Thus, PASA or the related method of PAMSA may be used to specifically amplify the mutation sequences of the invention. Where such amplification is done on genetic material (or RNA) obtained from an individual, it can serve as a method of detecting the presence of the mutations.

As mentioned above, a method known as ligase chain reaction (LCR) can be used to successfully detect a single-base substitution (29, 30). LCR probes may be combined or multiplexed for simultaneously screening for multiple different mutations. Thus, LCR can be particularly useful where multiple mutations are predictive of the same disease.

Finally, the Parkinson's disease mutation of the present invention may also be detected using chain termination with labeled dideoxynucleotides. For instance, U.S. Pat. No. 5,047,519 to Hobbs et al. discloses fluorescently-labeled nucleotides as chain-terminating substrates for a fluorescence-based DNA sequencing method. With such substrates and knowledge of the gene sequence of interest, it is possible to design an assay using a gene-specific primer to initiate a polymerase reaction immediately flanking the position of the mutation, employing color-coded dideoxynucleotide terminators such that the specific nucleotide at the position of the mutation may be easily determined via a calorimetric assay.

Transgenic Animals and Cell Lines

Having identified subjects having a predisposition to Parkinson's disease associated with a specific mutation, the subjects can participate in the screening of putative agents capable of treating Parkinson's disease. This method comprises administering the test agent to the subject, which may be a human, which has a mutation in a gene associated with Parkinson's disease and monitoring the effect of the agent on the subject's condition. If the symptoms of Parkinson's disease improve, the agent can be used as a treatment for the disease.

In addition, it is possible to develop transgenic model systems and/or cell lines containing the mutated nucleic acid(s) for use, for example, as model systems for screening for drugs and evaluating drug efficiency. Additionally, such model systems provide a tool for defining the underlying biochemistry of, for instance, the mutated synuclein gene, thereby providing a rationale for drug design.

One approach to creating transgenic animals is to mutate the animal gene of interest by in vivo mutagenesis, transfer the mutant gene into embryonic stem cells by DNA transfection and inject the embryonic stem cells into blastocysts in order to retrieve offspring which carry the disease-causing mutation (31). Alternatively, the technique of microinjection of the mutated gene, into a one-cell embryo followed by incubation in a foster mother can be used. Alternatively, viral vectors, e.g., Adeno-associated virus, can be used to deliver the mutated gene to a stem cell, or may be used to target specific cells of a fully developed animal (32, 33).

Antibodies and Recombinant Expression of Polypeptides

When the mutated gene product is a polypeptide, e.g. the 209 mutation, it can be used to prepare antisera and monoclonal antibodies using, for example, the method of Kohler and Milstein (34). Such monoclonal antibodies could then form the basis of a diagnostic test, or may even be useful in therapies directed toward inhibiting the action of the mutant protein in a patient with Parkinson's disease.

Mutant polypeptides can also be used to immunize an animal for the production of polyclonal antiserum (35). For example, a recombinantly produced fragment of a variant polypeptide can be injected into a mouse along with an adjuvant so as to generate an immune response. Murine immunoglobulins which specifically bind the recombinant fragment can be harvested from the immunized mouse as an antiserum, and may be further purified by affinity chromatography or other means. Additionally, spleen cells are harvested from the mouse and fused to myeloma cells to produce a bank of antibody-secreting hybridoma cells, which can then be screened for clones that secrete immunoglobulins which bind the recombinantly produced fragment with an increased affinity. More specifically, immunoglobulins that selectively bind to the variant polypeptides but poorly or not at all to wild-type polypeptides are selected, either by pre-absorption with wild-type proteins or by screening of hybridoma cell lines for specific idiotypes that bind the variant but not wild-type.

These antibodies can be used to screen protein and tissue samples for the presence of mutated proteins. A colored enzymatic reaction occurs when the specific antibody remains bound to its target protein, in situ, after thorough washing, as directed by established protocols.

Gene expression

The nucleic acid sequences of the present invention will be capable of expressing the desired mutant or normal polypeptides in an appropriate host cell. For expression in host cells, the DNA sequences of the present invention will be operably linked to, i.e., positioned to ensure the functioning of, an expression control sequence. For example, such polynucleotides can include a promoter, a transcription termination site (polyadenylation site in eukaryotic expression hosts), a ribosome binding site, and, optionally, an enhancer for use in eukaryotic expression hosts. In addition, the DNA sequence of the present invention may also be fused such that the reading frame is conserved to an appropriate signal sequence to facilitate export of the encoded protein across the cell membrane.

Expression vectors are typically replicable in the host organisms either as episomes or as an integral part of the host chromosomal DNA. A variety of suitable expression vectors are disclosed in Sambrook et al. (13). Commonly, expression vectors will contain selection markers, e.g., tetracycline resistance or hygromycin resistance, to permit detection and/or selection of those cells transformed with the desired DNA sequences.

*E. coli* is one prokaryotic host that is particularly useful for cloning and expression of the DNA sequences of the present invention because of the wide variety of available expression systems. Vectors suitable for use in *E. coli* are known and are commercially available, i.e. pBR322 (13), pBLUESCRIPT (Stratagene), etc. Also, a variety of different types of expression systems may be used, including plasmids, cosmids, bacteriophage lambda, etc. Other microbial hosts suitable for use include bacilli, such as *Bacillus subtilus*, and other enterobacteriaceae, such as *Salmonella, Serratia*, and various *Pseudomonas* species. Expression vectors for use in prokaryotic host cells will typically contain expression control sequences compatible with the host cell (e.g., an origin of replication). In addition, any of a variety of well-known promoters may be used, such as the lactose promoter system, a tryptophan (Trp) promoter system, a beta-lactamase promoter system, or a promoter system from phage lambda. A promoter may optionally contain an operator sequence for regulatable gene expression, and will have a ribosome binding site sequence for the initiation of translation.

In addition to microorganisms, mammalian tissue cell culture may also be used to express and produce the polypeptides of the present invention (36). Vectors for use in eukaryotic cells are known and commercially available, i.e. pcDNA3 (Invitrogen). Eukaryotic cells are actually preferred, and a number of suitable host cell lines capable of secreting intact human proteins have been developed in the art, including CHO cells, COS cells, HeLa cells, myeloma cell lines, Jurkat cells, etc. Promoters for use in eukaryotic vectors may be cell-specific, or capable of being expressed in a wide variety of cells, i.e. viral promoters.

Expression vectors of the present invention (e.g., comprising nucleic acid sequences encoding a mutant or normal polypeptide) can be transferred into the host cell by well-known methods, which vary depending on the type of cellular host. For example, calcium chloride transfection is commonly utilized for prokaryotic cells, whereas calcium phosphate treatment or electroporation may be used for other cellular hosts.

Kits

The method lends itself readily to the formulation of test kits which can be utilized in diagnosis. Such a kit would comprise a carrier compartmentalized to receive in close confinement one or more containers wherein a first container may contain suitably labeled DNA probes. Other containers may contain reagents useful in the localization of the labeled probes, such as enzyme substrates. Still other containers may contain restriction enzymes (such as Tsp45I), buffers, etc., together with instructions for use.

DESCRIPTION OF THE INVENTION

Detailed Description of the Preferred Embodiments

The following laboratory procedures were used:

DNA samples were collected upon informed consent. High molecular witht genomic DNA was isolated from whole-blood lysate by methods previously described (39). Pairwise likage analysis was performed using the MLINK program of the FASTLINK package (40–42). Allele frequencies were used as reported in the Genomic Data Base and the Cooperative Human Linkage Consortium (CHLC) database. Multipoint analysis was performed using the LINKMAP program of the FASTLINK package. For the multipoint analysis allele frequencies were set to 1/n where n equals the number of alleles observed. In the two point analysis LOD scores were calculated for both the reported and the 1/n allele frequencies with minmal effect on the maximum LOD score abserved. Simulations of multipoint analysis in a subset of the pedigree with different allele frequencies similarly indicated no significant effect on the scores calculated. Maximum LOD scores as shown were observed for the heterozygote and homozygote disease allele penetrance set to 0.99, which is similar to the PD allele penetrance previously reported ranging from 0.88 to 0.94 (3). All unaffected individuals used in the study were of age above the man for onset of illness. Disease allele frequency was set to 0.0001. Distances and order of genetic markers were set as reported in the CHLC database. Overlapping three point analysis was performed for markers D4S2361, D4S1647, D4S421 and the PD locus. The 12 allele D4S2380 locus was not included because of prohibitive time run. Multipoint analysis was performed on an IBM SP2 parallel computer and the SCI Challenge machine.

For mutation analysis genomic DNA was amplified with oligonucleotides (3): 5'GCTAATCAGCAATTTAAG-GCTAG 3' and (13): 5' gatatgttcttagatgctcag (SEQ ID NO:3) of genbank ID: U46898, under standard PCR conditions. Sequence analysis was performed using the Perkin Elmer dye terminator cycle sequencing kit on an ABI 373 fluorescent sequencer (ABI, Foster City, Calif.). Restriction digestion was performed following the PCR with Tsp45 I according to manufacturer's protocol (New England Biolabs, Beverly. MA). The digested PCR products were electrophoresed on a 6% Visigel (Stratagene, La Jolla. CA), and visualized by ethidium bromide staining. Pedigree structure in FIG. 2 has been slightly modified in order to protect patient confidentiality. Total RNA was extracted from the lymphoblastoid cell line of an affected individual and first strand synthesis was performed by oligo dT priming (Gibco BRL, Gaithersburg, Md.). Primers (1F) 5' ACGACAGT-GTGGTGTAAAGG 3' and (13R) 5' aacatctgtcagcagatctc 3' (SEQ ID NO: 10) corresponding to nucleotides 21–40 and 520–501 of genbank L08850 were used to amplify a product of 500 bp containing the mutation at nucleotide 209. PCR products were subjected to restriction digestion by Tsp45 I. The nucleotide at nt 209 creates a novel Tsp45 I site (FIG. 1), so that the normal allele will be restricted in 4 fragments of 249, 218, 24 and 9 bp, where the mutant allele will have 5 fragments of 249, 185, 33, 24 and 9 bp of size, as shown in FIG. 3. Size standards used, where the 100 bp ladder (Gibco BRL, Gaithersburg, Md.).

EXAMPLE 1

Figure 5:
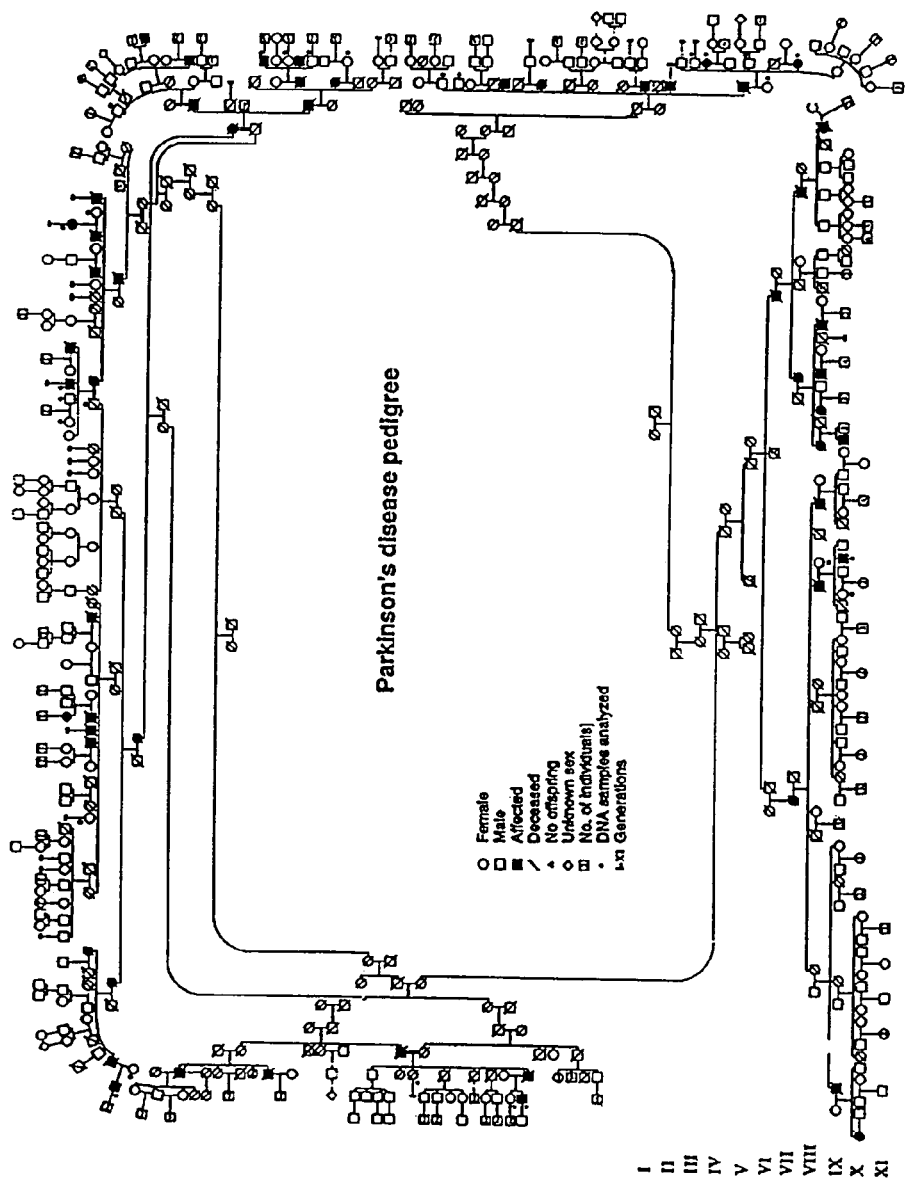

In an effort to identify a genetic locus responsible for Parkinson's disease, we performed a genome scan in a large kindred of Italian descent with pathologically confirmed PD (FIG. 5). The kindred originated in the town of Contursi in the Salerno province of Southern Italy (3). Some members emigrated to the United States, Germany and other countries. The extended family pedigree consists of 592 members with 60 individuals affected by PD. The average age of onset for the illness in this pedigree (FIG. 5) has been shown to be 46 Å 13 years. One hundred and fourty genetic markers were typed in this pedigree at an average spacing of about 20 cm. Genetic markers at the cytogenetic location 4q21–q23 were the only ones to show linkage to the disease phenotype with a Zmax=6.00 at theta=0.00 for marker D4S23801 (see Table 1).

TABLE 1

Two point LOD scores between chromosome 4q markers and the PD locus
Two-point LOD scores at recombination fractions of:

| | Locus | | | | | | | | |
|---|---|---|---|---|---|---|---|---|---|
| | 0.00 | 0.01 | 0.05 | 0.10 | 0.20 | 0.30 | 0.40 | $Z_{max}$ | $\theta_{max}$ |
| D4S2361 | −5.60 | −0.83 | 0.30 | 0.54 | 0.43 | 0.21 | 0.06 | 0.55 | 0.12 |
| D4S2380 | 6.00 | 5.90 | 5.30 | 4.60 | 3.00 | 1.50 | 0.50 | 6.00 | 0.00 |
| D4S1647 | 5.22 | 5.07 | 4.47 | 3.71 | 2.26 | 1.05 | 0.30 | 5.22 | 0.00 |
| D4S421 | −2.42 | 0.45 | 0.77 | 0.65 | 0.38 | 0.22 | 0.09 | 0.77 | 0.05 |

Recombinations between the disease phenotype and genetic markers were observed in the proximal region for marker D4S2361 and in the distal region for marker D4S421. Genetic markers D4S2380 and D4S1647 showed no obligate recombination events in the affected individuals.

Figure 6:
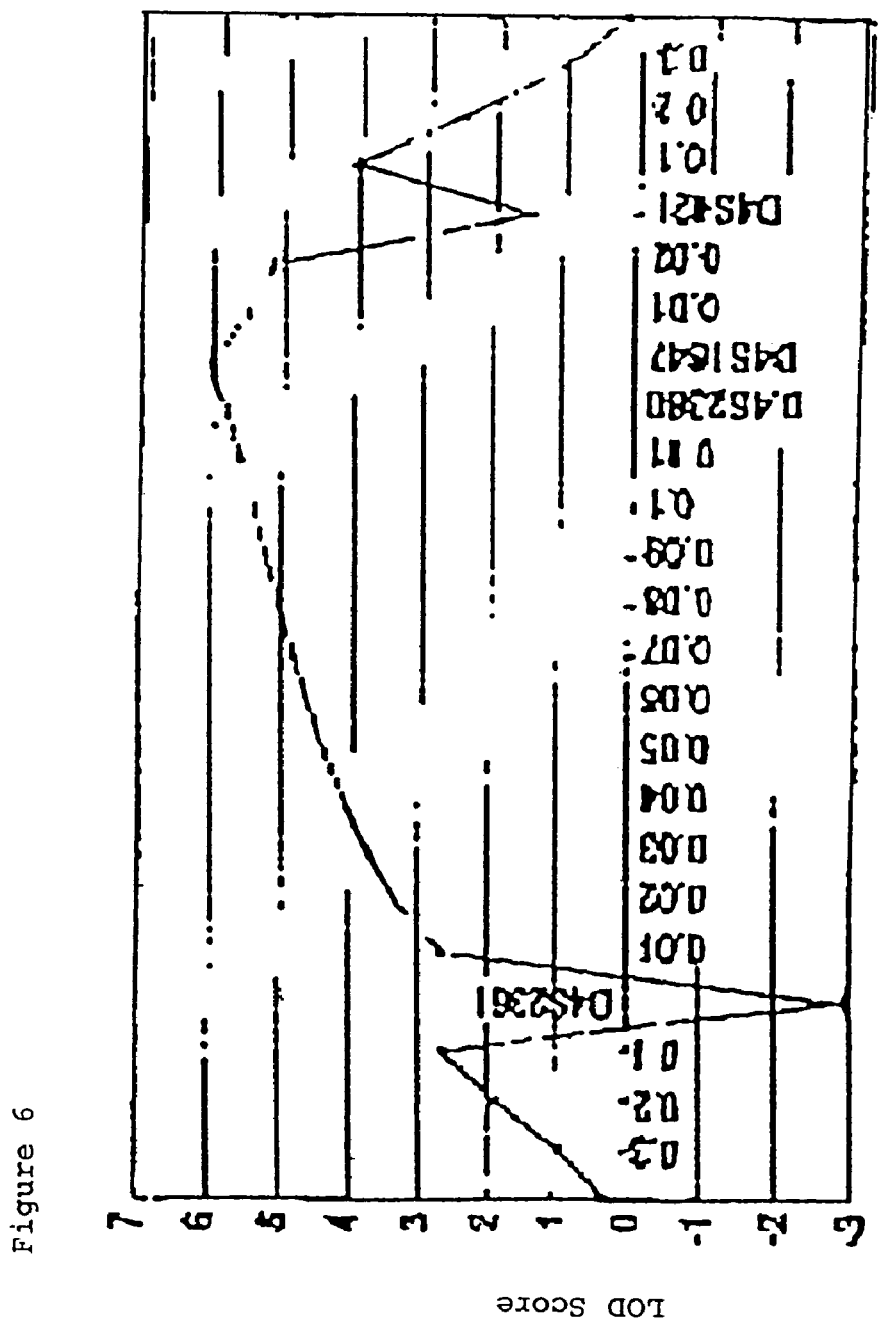

Multipoint LOD score analysis between markers D4S2361-13cM–D4S1647-3cM–D4S421 and the disease locus places the PD gene between markers D4S2361 and D4S421 at a recombination distance of 0.00 cM from marker D4S1647 with a Zmax=6.04 (FIG. 6). This location is favored from the alternative genetic intervals by a difference in the LOD score of greater than three LOD units.

Although expansions of unstable trinucleotide repeats are found in a number of human neurogenerative conditions, there is no evidence for an association of a CAG trinucleotide repeat expansion in families with PD (43). In addition, genetic linkage studies in other families with PD-like illnesses do not support the involvement of several candidate genes (glutathione peroxidase, tyrosine hydroxylase, brain-derived neurotrophic factor, catalase, amyloid precursor protein, CuZn superoxide dismutase and debrisoquinone 4-hydroxylase) in the etiology of the disorder (44). Genes previously mapped in the general region of linkage include the loci for alcohol dehydrogenase, formaldehyde dehydrogenase, synuclein, UDP-N-acetylglycosamine phosphotransferase and others.

Our localization of a PD susceptibility gene represents the first genetic locus linked to PD. Other distinct clinicopathological entities associated with parksonian features are probably linked to other genetic loci. For example, Wilhelmsen-Lynch disease (disinhibition-dementia-parkinsonian-amyotrophy complex) is linked to the 17q21–q22 chromosomal region (45). If the pathogenesis of diseases affecting the nigrostriatal pathway includes environmental influences, then a range of mutations affecting vulnerable sites in the electron transport chain or enzyme polymorphisms influencing neurotoxin metabolism may vary the penetrance of PD by altering an individual's resistance to exogenous or endogenous agents. However, our finding of a highly penetrant genetic locus linked to PD suggested that abnormalities of a single gene may be sufficient to cause Parkinson's disease.

EXAMPLE 2

In an effort to identify a specific gene between markers D4S2361 and D4S421 that is associated with predisposition to Parkinson's disease, we conducted sequence analysis of 5 candidate genes in this region.

Alpha synuclein, a presynaptic nerve terminal protein, was originally identified as the precursor protein for the NAC peptide, a non beta amyloid component of Alzheimer's disease (AD) amyloid plaques (4). The human alpha synuclein gene was previously mapped in the 4q21–q22 region (5). We refined the mapping, and determined that the alpha synuclein gene is located within the non-excluded region harboring the PD gene in the Italian kindred. Thus alpha synuclein represented an excellent candidate locus for PD.

Figures 2, 3:
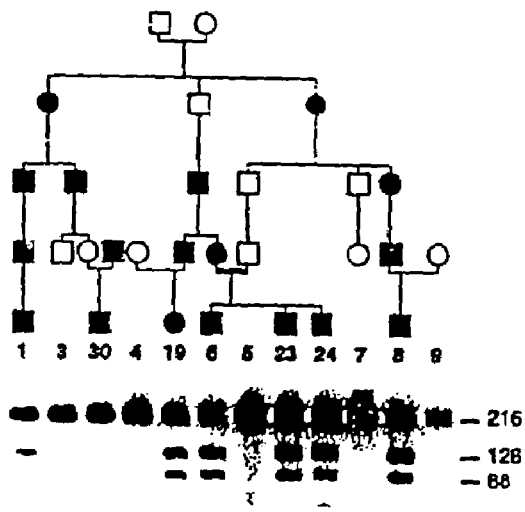
Figure 4:
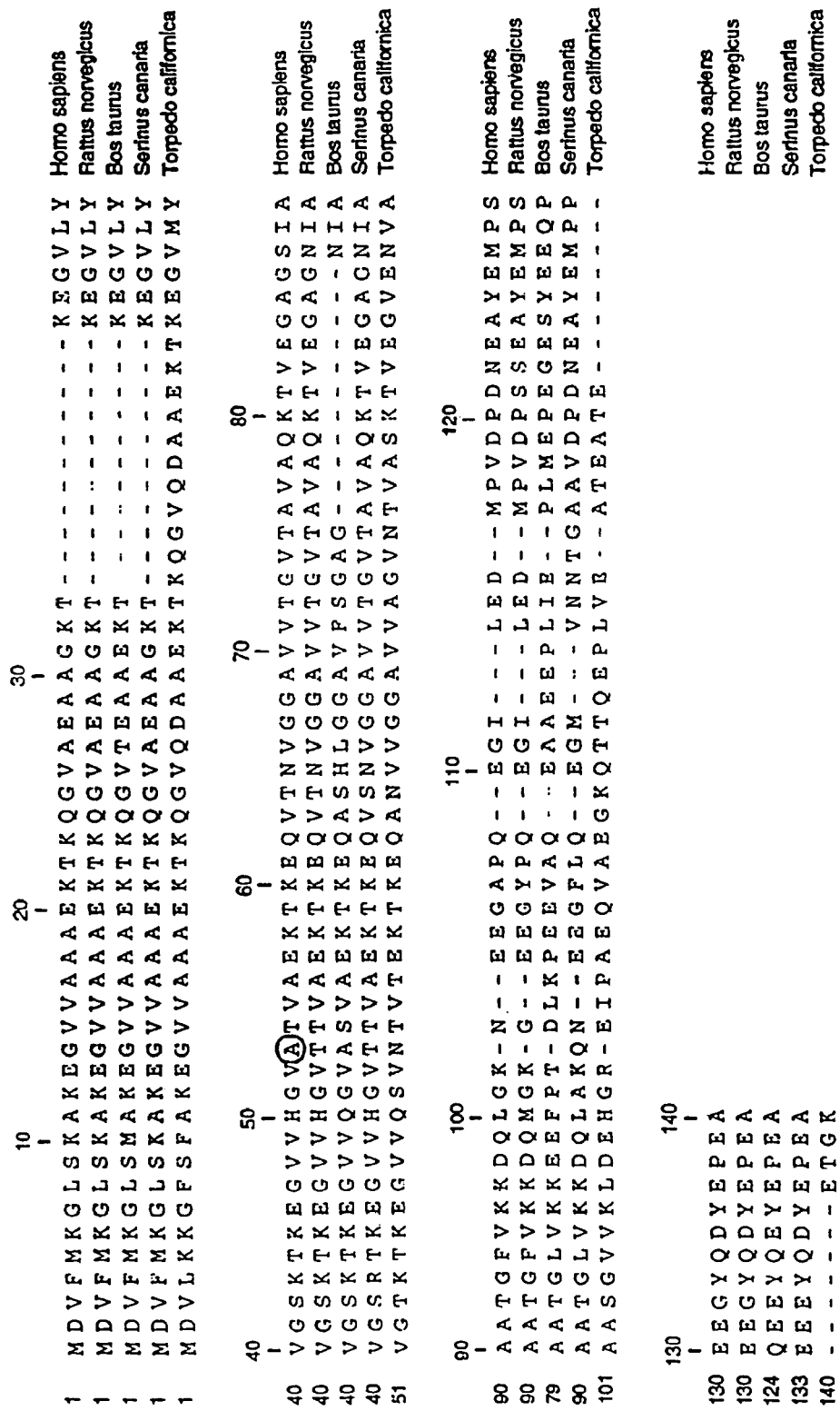

Sequence analysis of the fourth exon of the alpha synuclein gene revealed a single base pair G209A change from the published sequence of the gene (GenBank ID L08850), which results in an Ala53Thr substitution and the creation of a novel Tsp45 I restriction site (FIG. 1). Mutation analysis for the G209A change in the Italian kindred shows complete segregation with the PD phenotype with exception of individual 30 (FIG. 2), who is affected but not carrying this mutation. This individual apparently inherited a different PD mutation from his father, as we have shown that he shares a genetic haplotype with his unaffected maternal uncle, individual 3, for genetic markers in the PD linkage region.

The frequency of this variation was studied in two general population samples, one consisting of 120 chromosomes of the parents of the CEPH reference families, and the other consisting of 194 chromosomes of unrelated individuals from the blood bank in Salerno, Italy, a city near the town from which the family originated. Of these 314 general population chromosomes none was found to carry the G209A mutation. Fifty two patients of Italian descent with sporadic PD were also screened for the mutation (FIG. 2), along with 5 probands from previously unpublished Greek families with PD. The Ala53Thr change was found to be present in three of the Greek kindreds and it segregated with the PD phenotype. In those three Greek kindreds it is worth noting that the age of onset for the disease is relatively early, ranging from the mid 30's to the mid 50's. Extended haplotype analysis of the Greek kindreds and the Italian PD family suggests that the mutations arose independently on different ancestral chromosomes. The finding of the Ala53Thr substitution in four independent PD families and its absence from 314 control chromosomes provides the strongest genetic evidence that this mutation in the human alpha synuclein gene is causative for the PD phenotype in these families.

We have also demonstrated by RT PCR that the mutant allele is transcribed in the lymphoblast cell line of an affected individual from the Italian kindred (FIG. 3) (7). Thus, it is reasonable to assume that the mutant protein is indeed expressed.

EXAMPLE 3

Since homologous genes that are related to the alpha synuclein protein have been identified in other species, it seemed reasonable to assume that homologues of alpha synuclein would exist in humans as well. In fact, human beta synuclein has previously been described (46), and is approximately 60' similar to alpha synuclein at the protein level.

We set out to identify other related homologues by searching various databases for homologous genes and proteins. Protein sequence databases searched included the NR (non-redundant) and "month" databases of Genbank and Swiss Prot. Nucleotide databases included NR, month, dbstf, GSS (Genome Sequence Service) and EPD (eurkaryotic Promoter Database). Several human clones were identified and characterized as alpha, beta and gamma clones as shown in FIG. 7. Potential gamma clones were identified on the basis of homology to known rat and mouse sequences. Although gamma synuclein has been identified in species other than human, this is the first identification of the corresponding gamma synuclein from humans.

Using two primers sets designed from known database sequences, (5'ATGTCTTCAAGAAGGGCTTC3' (SEQ ID NO:20); 5'CCTTGGTCTTCTCAGCTGCT3' (SEQ ID NO:21) and 5'AGCGTGGATGACCTGAAGAG3' (SEQ ID NO:22); 5'AGCACAGGTGGACAGGCCAAG3' (SEQ ID NO:23)), we have isolated two BAC clones, 139A20 and 174P13, from a Genome System commercial Bacterial Artificial Chromosome library (St. Louis, Mo.) which contain the human beta and gamma synuclein genes, respectively. The beta gene contained one clone 139A20 has been sequenced as shown in FIG. 8 (SEQ ID NO:11), which contains all coding exon sequences and some additional non-coding intronic sequence. The gamma clone 174P13 has been sequenced and is available in GenBank: accession number AF044311. Sequence from the 5' end is given in FIG. 9 (SEQ ID NO:12 NO:12), and the sequence from the 3' end is given in FIG. 10 (SEQ ID NO:13 NO:13). The human alpha synuclein gee has also been sequenced as shown in FIG. 11, which provides the sequence of each separate exon region with some additional flanking intronic sequence for each exon (SEQ ID NOS:14–19).

REFERENCES

Each of the following citations is herein incorporated by reference:

U.S. Patents 5,494,794 Wallace Feb. 27, 1996
5,047,519 Hobbs, Jr. et al. Sep. 10, 1991

OTHER REFERENCES

1. J. Parkinson, An Essay on the Shaking Palsy (Whitingham and Rowland, London, 1817); W. R. Cowers, *A Manual of Diseases of the Nervous System*, 2nd ed. (Blakinston, Philadelphia, 1893), pp. 6366–6657.
2. A. M. Lazarrini et al., *Neurology* 44, 499 (1994).
3. L. I. Golbe et al., *Ann. Neurology* 27, 276 (1990); M. H Polymeropoulos et al., *Science* 274,1197 (1996).
4. K. Uéda et al., *Proc. Natl. Acad. Sci. U.S.A.* 90, 11282 (1993).
5. X. Chen et al., *Genomics* 26, 425 (1995); Y. Shitasaki et al., *Cytogenet. Cell. Genet.* 71, 54 (1995).
6. A. Iwai et al., *Biochemistry* 15, 10139 (1995); P. H. Weinreb et al., *Biochemistry* 29, 13709 (1996); P. H. Jensen et al., *Biochem J* 15, 91(1995); P. H. Jensen et al., *Biochem. J.* 323, 539 (1997).
7. L. Maroteaux and R. H. Scheller, *Brain Res. Mol. Brain. Res.* 11, 335 (1991).
8. R. L. Doty et al., *Ann. Neurol.* 32, 97 (1992); R. K. Pearce, C. H. Hawkes, S. E. Daniel *Mov. Disord.* 10, 283 (1995).
9. J. M. George et al., *Neuron* 15, 361 (1995).

10. L. Maroteaux, J. T. Campanelli, R. H. Scheller J. Neurosci. 8, 2804 (1988).
11. Alzheimer's Disease Collaborative *Group Nature Genet.* 11, 219 (1995); J. Perez-Tur et al., *NeuroReport* 7, 297 (1995); R. Sherrington et al., *Nature* 375, 754 (1995); S. Sorbi et al., *Lancet* 346, 439 (1995); W. Wasco et al., *Nature Med* 1, 848 (1995); E. Levy-Lahad et al., *Science* 269, 970 (1995); E. I. Rogaev et al., *Nature* 376, 775 (1995).
12. Hsiao K et al., *Nature* 338, 342 (1989).
13. Maniatis et al. (1989) Molecular Cloning: A Laboratory Manual, 2nd Ed., Cold Spring Harbor Laboratory, Cold Spring Harbor, N.Y.
14. Berger and Kimmel (1987) "Guide to Molecular Cloning Techniques," Methods in Enzymology, Volume 152, Academic Press, Inc., San Diego, Calif.
15. Gibbs et al. (1989) Nucleic Acids Res. 17:2437.
16. Kwok et al. (1990) Nucleic Acids Res. 18:999.
17. Miyada et al. (1987) Methods Enzymol. 154:94.
18. Dihella et al. (1988) Lancet 1:497.
19. Promega Protocols and Applications Guide (1991) Promega Corporation, Madison, Wis.
20. Orita et al. (1989) Genomics 5:874–879.
21. Orita et al. (1990) Genomics 6:271–276.
22. Newton et al. (1989) Nucleic Acids Res. 17:2503.
23. Nichols et al. (1989) Genomics 5:535.
24. Okayama et al. (1989) J. Lab. Clin. Med. 114:105.
25. Sarkar et al. (1990) Anal. Blochem. 186:64.
26. Sommer et al. (1989) Mayo Clin. Proc. 64:1361.
27. Wu (1989) Proc. Natl. Acad. Sci. (U.S.A.) 86:2757
28. Dutton et al. (1991) Biotechniques 11:700.
29. Baany et al. (1991) Proc. Natl. Acad. Sci. (U.S.A.) 88:189.
30. R. A. Weiss (1991) Science 254:1992.
31. Frohman and Martin, Cell (1989) 56:145.
32. Mendelson et al. Virology 166:154–165.
33. Wondisford et al. (1988) Molec. Endocrinol. 2:32–39 (1988).
34. Kohler and Milstein, (1975) Nature 256:495–497.
35. Antibodies: A Laboratory Manual, Harlow and Lane (1988), Cold Spring Harbor Laboratory, Cold Spring Harbor, N.Y.
36. Winacker (1987) "From Genes to Clones," VCH Publishers, New York, N.Y.).
37. Quenn et al. (1986) Immunol. Rev. 89:49–68.
38. Bell et al. (1981) Proc. Natl. Acad. Sci. USA 78: 5759.
39. Gyapay et al. (1994) Nature Genet. 7: 262.
40. Lathrop et al. (1984) Proc. Natl. Acad. Sci USA 81: 3442.
41. Cottingham et al. (1984) Am. J. Hum. Genet. 54: 252.
42. Gupta et al. (1995) Comp. Biomed. Res. 28: 116.
43. Carrero-Valenzuela et al. (1995) Neurology 45: 1760; M. H. Polymeropoulus, data not shown.
44. Gasser et al. (1994) Ann. Neurol. 36: 387.
45. Lynch et al. (1994) Neurology 44: 1878.
46. Jakes et al. (1994) Febs Letts. 345: 27–32.
47. Polymeropoulos et al. (1997) Science 276:2045–2047, which is relied upon and hereby expressly incorporated by reference herein.
48. Lavedan et al. (1998) in press, which is relied upon and hereby expressly incorporated by reference herein.

What is claimed is:

1. An isolated nucleic acid comprising a nucleotide sequence encoding a mutated human alpha synuclein protein having a mutation at position 209 wherein a guanine is replaced by an adenine.

2. An isolated nucleic acid comprising the sequence given in SEQ ID NO. 1.

3. A vector comprising the isolated nucleic acid of claim 1.

4. An isolated host cell comprising the vector of claim 3.

5. A method of detecting subjects at increased risk for Parkinson's Disease, comprising:

obtaining a sample comprising nucleic acids from the subjects; and detecting in the nucleic acids the presence of the nucleic acid of claim 1, thereby identifying subjects at increased risk for Parkinson's Disease.

6. A method of detecting subjects at increased risk for Parkinson's Disease, comprising:

obtaining a sample comprising nucleic acids from the subjects; and detecting in the nucleic acids the presence of the nucleic acid of claim 2, thereby identifying subjects at increased risk for Parkinson's Disease.

* * * * *

SEQUENCE LISTING

```
<160> NUMBER OF SEQ ID NOS: 25

<210> SEQ ID NO 1
<211> LENGTH: 216
<212> TYPE: DNA
<213> ORGANISM: Homo sapiens
<220> FEATURE:
<221> NAME/KEY: modified_base
<222> LOCATION: (133)
<223> OTHER INFORMATION: a, t, c, g, other or unknown
<221> NAME/KEY: CDS
<222> LOCATION: (56)..(97)

<400> SEQUENCE: 1
gctaatcagc aatttaaggc tagcttgaga cttatgtctt gaatttgttt ttgta ggc      58
                                                                Gly
                                                                  1 tcc aaa acc aag gag gga gtg gtg cat ggt gtg aca aca ggtaagctcc      107
Ser Lys Thr Lys Glu Gly Val Val His Gly Val Thr Thr
          5                   10 attgtgctta tatcaaagat gatatntaaa gtatctagtg attagtgtgg cccagtatca   167
agattcctat gaaattgtaa aacaatcact gagcatctaa gaacatatc                216

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 2
```

-continued

```
gctaatcagc aatttaggct ag                                    22
```

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 3

```
ctatacaaga atctacgagt c                                     21
```

<210> SEQ ID NO 4
<211> LENGTH: 393
<212> TYPE: PRT
<213> ORGANISM: Homo sapiens

<400> SEQUENCE: 4

```
Met Glu Thr Ala Ser Pro Val Ala Leu Pro His Glu Met Glu Thr Leu
  1               5                  10                  15

Tyr Ser Gly Leu Tyr Leu Glu Ser Glu Arg Leu Tyr Ser Ala Leu Ala
             20                  25                  30

Leu Tyr Ser Gly Leu Gly Leu Tyr Val Ala Leu Val Ala Leu Ala Leu
         35                  40                  45

Ala Ala Leu Ala Ala Leu Ala Gly Leu Leu Tyr Ser Thr His Arg Leu
     50                  55                  60

Tyr Ser Gly Leu Asn Gly Leu Tyr Val Ala Leu Ala Leu Ala Gly Leu
 65                  70                  75                  80

Ala Leu Ala Ala Leu Ala Gly Leu Tyr Leu Tyr Ser Thr His Arg Leu
                 85                  90                  95

Tyr Ser Gly Leu Gly Leu Tyr Val Ala Leu Leu Glu Thr Tyr Arg Val
            100                 105                 110

Ala Leu Gly Leu Tyr Ser Glu Arg Leu Tyr Ser Thr His Arg Leu Tyr
        115                 120                 125

Ser Gly Leu Gly Leu Tyr Val Ala Leu Val Ala Leu His Ile Ser Gly
    130                 135                 140

Leu Tyr Val Ala Leu Ala Leu Ala Thr His Arg Val Ala Leu Ala Leu
145                 150                 155                 160

Ala Gly Leu Leu Tyr Ser Thr His Arg Leu Tyr Ser Gly Leu Gly Leu
                165                 170                 175

Asn Val Ala Leu Thr His Arg Ala Ser Asn Val Ala Leu Gly Leu Tyr
            180                 185                 190

Gly Leu Tyr Ala Leu Ala Val Ala Leu Val Ala Leu Thr His Arg Gly
        195                 200                 205

Leu Tyr Val Ala Leu Thr His Arg Ala Leu Ala Val Ala Leu Ala Leu
    210                 215                 220

Ala Gly Leu Asn Leu Tyr Ser Thr His Arg Val Ala Leu Gly Leu Gly
225                 230                 235                 240

Leu Tyr Ala Leu Ala Gly Leu Tyr Ser Glu Arg Ile Leu Glu Ala Leu
                245                 250                 255

Ala Ala Leu Ala Ala Leu Ala Thr His Arg Gly Leu Tyr Pro His Glu
            260                 265                 270

Val Ala Leu Leu Tyr Ser Leu Tyr Ser Ala Ser Pro Gly Leu Asn Leu
        275                 280                 285

Glu Gly Leu Tyr Leu Tyr Ser Ala Ser Asn Gly Leu Gly Leu Gly Leu
    290                 295                 300
```

```
Tyr Ala Leu Ala Pro Arg Gly Leu Asn Gly Leu Gly Leu Tyr Ile Leu
305                 310                 315                 320

Glu Leu Glu Gly Leu Ala Ser Pro Met Glu Thr Pro Arg Val Ala Leu
            325                 330                 335

Ala Ser Pro Pro Arg Ala Ser Pro Ala Ser Asn Gly Leu Ala Leu Ala
            340                 345                 350

Thr Tyr Arg Gly Leu Met Glu Thr Pro Arg Ser Glu Arg Gly Leu Gly
            355                 360                 365

Leu Gly Leu Tyr Thr Tyr Arg Gly Leu Asn Ala Ser Pro Thr Tyr Arg
370                 375                 380

Gly Leu Pro Arg Gly Leu Ala Leu Ala
385                 390

<210> SEQ ID NO 5
<211> LENGTH: 394
<212> TYPE: PRT
<213> ORGANISM: Rattus norvegicus

<400> SEQUENCE: 5

Met Glu Thr Ala Ser Pro Val Ala Leu Pro His Glu Met Glu Thr Leu
 1               5                  10                  15

Tyr Ser Gly Leu Tyr Leu Glu Ser Glu Arg Leu Tyr Ser Ala Leu Ala
            20                  25                  30

Leu Tyr Ser Gly Leu Gly Leu Tyr Val Ala Leu Val Ala Leu Ala Leu
            35                  40                  45

Ala Ala Leu Ala Ala Leu Ala Gly Leu Leu Tyr Ser Thr His Arg Leu
        50                  55                  60

Tyr Ser Gly Leu Asn Gly Leu Tyr Val Ala Leu Ala Leu Ala Gly Leu
65                  70                  75                  80

Ala Leu Ala Ala Leu Ala Gly Leu Tyr Leu Tyr Ser Thr His Arg Leu
            85                  90                  95

Tyr Ser Gly Leu Gly Leu Tyr Val Ala Leu Leu Glu Thr Tyr Arg Val
            100                 105                 110

Ala Leu Gly Leu Tyr Ser Glu Arg Leu Tyr Ser Thr His Arg Leu Tyr
            115                 120                 125

Ser Gly Leu Gly Leu Tyr Val Ala Leu Val Ala Leu His Ile Ser Gly
        130                 135                 140

Leu Tyr Val Ala Leu Thr His Arg Thr His Arg Val Ala Leu Ala Leu
145                 150                 155                 160

Ala Gly Leu Leu Tyr Ser Thr His Arg Leu Tyr Ser Gly Leu Gly Leu
            165                 170                 175

Asn Val Ala Leu Thr His Arg Ala Ser Asn Val Ala Leu Gly Leu Tyr
            180                 185                 190

Gly Leu Tyr Ala Leu Ala Val Ala Leu Val Ala Leu Thr His Arg Gly
            195                 200                 205

Leu Tyr Val Ala Leu Thr His Arg Ala Leu Ala Val Ala Leu Ala Leu
            210                 215                 220

Ala Gly Leu Asn Leu Tyr Ser Thr His Arg Val Ala Leu Gly Leu Gly
225                 230                 235                 240

Leu Tyr Ala Leu Ala Gly Leu Tyr Ala Ser Asn Ile Leu Glu Ala Leu
            245                 250                 255

Ala Ala Leu Ala Ala Leu Ala Thr His Arg Gly Leu Tyr Pro His Glu
            260                 265                 270

Val Ala Leu Leu Tyr Ser Leu Tyr Ser Ala Ser Pro Gly Leu Asn Met
```

```
                      275                 280                 285
Glu Thr Gly Leu Tyr Leu Tyr Ser Gly Leu Tyr Gly Leu Gly Leu Gly
    290                 295                 300

Leu Tyr Thr Tyr Arg Pro Arg Gly Leu Asn Gly Leu Gly Leu Tyr Ile
305                 310                 315                 320

Leu Glu Leu Glu Gly Leu Ala Ser Pro Met Glu Thr Pro Arg Val Ala
                325                 330                 335

Leu Ala Ser Pro Pro Arg Ser Glu Arg Ser Glu Arg Gly Leu Ala Leu
                340                 345                 350

Ala Thr Tyr Arg Gly Leu Met Glu Thr Pro Arg Ser Glu Arg Gly Leu
                355                 360                 365

Gly Leu Gly Leu Tyr Thr Tyr Arg Gly Leu Asn Ala Ser Pro Thr Tyr
            370                 375                 380

Arg Gly Leu Pro Arg Gly Leu Ala Leu Ala
385                 390

<210> SEQ ID NO 6
<211> LENGTH: 362
<212> TYPE: PRT
<213> ORGANISM: Bos taurus

<400> SEQUENCE: 6

Met Glu Thr Ala Ser Pro Val Ala Leu Pro His Glu Met Glu Thr Leu
  1               5                  10                  15

Tyr Ser Gly Leu Tyr Leu Glu Ser Glu Arg Met Glu Thr Ala Leu Ala
                 20                  25                  30

Leu Tyr Ser Gly Leu Gly Leu Tyr Val Ala Leu Val Ala Leu Ala Leu
             35                  40                  45

Ala Ala Leu Ala Ala Leu Ala Gly Leu Leu Tyr Ser Thr His Arg Leu
         50                  55                  60

Tyr Ser Gly Leu Asn Gly Leu Tyr Val Ala Leu Thr His Arg Gly Leu
 65                  70                  75                  80

Ala Leu Ala Ala Leu Ala Gly Leu Leu Tyr Ser Thr His Arg Leu Tyr
                 85                  90                  95

Ser Gly Leu Gly Leu Tyr Val Ala Leu Leu Glu Thr Tyr Arg Val Ala
            100                 105                 110

Leu Gly Leu Tyr Ser Glu Arg Leu Tyr Ser Thr His Arg Leu Tyr Ser
            115                 120                 125

Gly Leu Gly Leu Tyr Val Ala Leu Val Ala Leu Gly Leu Asn Gly Leu
        130                 135                 140

Tyr Val Ala Leu Ala Leu Ala Ser Glu Arg Val Ala Leu Ala Leu Ala
145                 150                 155                 160

Gly Leu Leu Tyr Ser Thr His Arg Leu Tyr Ser Gly Leu Gly Leu Asn
                165                 170                 175

Ala Leu Ala Ser Glu Arg His Ile Ser Leu Glu Gly Leu Tyr Gly Leu
                180                 185                 190

Tyr Ala Leu Ala Val Ala Leu Pro His Glu Ser Glu Arg Gly Leu Tyr
            195                 200                 205

Ala Leu Ala Gly Leu Tyr Ala Ser Asn Ile Leu Glu Ala Leu Ala Ala
        210                 215                 220

Leu Ala Ala Leu Ala Thr His Arg Gly Leu Tyr Leu Glu Val Ala Leu
225                 230                 235                 240

Leu Tyr Ser Leu Tyr Ser Gly Leu Gly Leu Pro His Glu Pro Arg Thr
                245                 250                 255
```

```
His Arg Ala Ser Pro Leu Glu Leu Tyr Ser Pro Arg Gly Leu Gly Leu
            260                 265                 270

Val Ala Leu Ala Leu Ala Gly Leu Asn Gly Leu Ala Leu Ala Ala Leu
        275                 280                 285

Ala Gly Leu Gly Leu Pro Arg Leu Glu Ile Leu Glu Gly Leu Pro Arg
        290                 295                 300

Leu Glu Met Glu Thr Gly Leu Pro Arg Gly Leu Gly Leu Tyr Gly Leu
305                 310                 315                 320

Ser Glu Arg Thr Tyr Arg Gly Leu Gly Leu Gly Leu Asn Pro Arg Gly
            325                 330                 335

Leu Asn Gly Leu Gly Leu Thr Tyr Arg Gly Leu Asn Gly Leu Thr Tyr
            340                 345                 350

Arg Gly Leu Pro Arg Gly Leu Ala Leu Ala
            355                 360

<210> SEQ ID NO 7
<211> LENGTH: 399
<212> TYPE: PRT
<213> ORGANISM: Serinus canaria

<400> SEQUENCE: 7

Met Glu Thr Ala Ser Pro Val Ala Leu Pro His Glu Met Glu Thr Leu
1               5                   10                  15

Tyr Ser Gly Leu Tyr Leu Glu Ser Glu Arg Leu Tyr Ser Ala Leu Ala
                20                  25                  30

Leu Tyr Ser Gly Leu Val Ala Leu Val Ala Leu Ala Leu Ala Ala Leu
            35                  40                  45

Ala Ala Leu Ala Gly Leu Leu Tyr Ser Thr His Arg Leu Tyr Ser Gly
        50                  55                  60

Leu Asn Gly Leu Tyr Val Ala Leu Ala Leu Ala Gly Leu Ala Leu Ala
65                  70                  75                  80

Ala Leu Ala Gly Leu Tyr Leu Tyr Ser Thr His Arg Leu Tyr Ser Gly
                85                  90                  95

Leu Gly Leu Tyr Val Ala Leu Leu Glu Thr Tyr Arg Val Ala Leu Gly
            100                 105                 110

Leu Tyr Ser Glu Arg Ala Arg Gly Thr His Arg Leu Tyr Ser Gly Leu
        115                 120                 125

Gly Leu Tyr Val Ala Leu Val Ala Leu His Ile Ser Gly Leu Tyr Val
        130                 135                 140

Ala Leu Thr His Arg Thr His Arg Val Ala Leu Ala Leu Ala Gly Leu
145                 150                 155                 160

Leu Tyr Ser Thr His Arg Leu Tyr Ser Gly Leu Gly Leu Asn Val Ala
                165                 170                 175

Leu Ser Glu Arg Ala Ser Asn Val Ala Leu Gly Leu Tyr Gly Leu Tyr
            180                 185                 190

Ala Leu Ala Val Ala Leu Val Ala Leu Thr His Arg Gly Leu Tyr Val
        195                 200                 205

Ala Leu Thr His Arg Ala Leu Ala Val Ala Leu Ala Leu Ala Gly Leu
210                 215                 220

Asn Leu Tyr Ser Thr His Arg Val Ala Leu Gly Leu Gly Leu Tyr Ala
225                 230                 235                 240

Leu Ala Gly Leu Tyr Ala Ser Asn Ile Leu Glu Ala Leu Ala Ala Leu
            245                 250                 255

Ala Ala Leu Ala Thr His Arg Gly Leu Tyr Leu Glu Val Ala Leu Leu
        260                 265                 270
```

```
Tyr Ser Leu Tyr Ser Ala Ser Pro Gly Leu Asn Leu Glu Ala Leu Ala
        275                 280                 285

Leu Tyr Ser Gly Leu Asn Ala Ser Asn Gly Leu Gly Leu Gly Leu Tyr
        290                 295                 300

Pro His Glu Leu Glu Gly Leu Asn Gly Leu Gly Leu Tyr Met Glu Thr
305                 310                 315                 320

Val Ala Leu Ala Ser Asn Ala Ser Asn Thr His Arg Gly Leu Tyr Ala
                325                 330                 335

Leu Ala Ala Leu Ala Val Ala Leu Ala Ser Pro Pro Arg Ala Ser Pro
                340                 345                 350

Ala Ser Asn Gly Leu Ala Leu Ala Thr Tyr Arg Gly Leu Met Glu Thr
                355                 360                 365

Pro Arg Pro Arg Gly Leu Gly Leu Gly Leu Thr Tyr Arg Gly Leu Asn
        370                 375                 380

Ala Ser Pro Thr Tyr Arg Gly Leu Pro Arg Gly Leu Ala Leu Ala
385                 390                 395

<210> SEQ ID NO 8
<211> LENGTH: 405
<212> TYPE: PRT
<213> ORGANISM: Torpedo californica

<400> SEQUENCE: 8

Met Glu Thr Ala Ser Pro Val Ala Leu Leu Glu Leu Tyr Ser Leu Tyr
  1               5                  10                  15

Ser Gly Leu Tyr Pro His Glu Ser Glu Arg Pro His Glu Ala Leu Ala
                 20                  25                  30

Leu Tyr Ser Gly Leu Gly Leu Tyr Val Ala Leu Val Ala Leu Ala Leu
             35                  40                  45

Ala Ala Leu Ala Ala Leu Ala Gly Leu Leu Tyr Ser Thr His Arg Leu
         50                  55                  60

Tyr Ser Gly Leu Asn Gly Leu Tyr Val Ala Leu Gly Leu Asn Ala Ser
 65                  70                  75                  80

Pro Ala Leu Ala Ala Leu Ala Gly Leu Leu Tyr Ser Thr His Arg Leu
                 85                  90                  95

Tyr Ser Gly Leu Asn Gly Leu Tyr Val Ala Leu Gly Leu Asn Ala Ser
                100                 105                 110

Pro Ala Leu Ala Ala Leu Ala Gly Leu Leu Tyr Ser Thr His Arg Leu
                115                 120                 125

Tyr Ser Gly Leu Gly Leu Tyr Val Ala Leu Met Glu Thr Thr Tyr Arg
            130                 135                 140

Val Ala Leu Gly Leu Tyr Thr His Arg Leu Tyr Ser Thr His Arg Leu
145                 150                 155                 160

Tyr Ser Gly Leu Gly Leu Tyr Val Ala Leu Val Ala Leu Gly Leu Asn
                165                 170                 175

Ser Glu Arg Val Ala Leu Ala Ser Asn Thr His Arg Val Ala Leu Thr
                180                 185                 190

His Arg Gly Leu Leu Tyr Ser Thr His Arg Leu Tyr Ser Gly Leu Gly
            195                 200                 205

Leu Asn Ala Leu Ala Ala Ser Asn Val Ala Leu Val Ala Leu Gly Leu
            210                 215                 220

Tyr Gly Leu Tyr Ala Leu Ala Val Ala Leu Val Ala Leu Ala Leu Ala
225                 230                 235                 240

Gly Leu Tyr Val Ala Leu Ala Ser Asn Thr His Arg Val Ala Leu Ala
```

-continued

```
                         245                 250                 255
Leu Ala Ser Glu Arg Leu Tyr Ser Thr His Arg Val Ala Leu Gly Leu
            260                 265                 270
Gly Leu Tyr Val Ala Leu Gly Leu Ala Ser Asn Val Ala Leu Ala Leu
        275                 280                 285
Ala Ala Leu Ala Ala Leu Ala Ser Glu Arg Gly Leu Tyr Val Ala Leu
    290                 295                 300
Val Ala Leu Leu Tyr Ser Leu Glu Ala Ser Pro Gly Leu His Ile Ser
305                 310                 315                 320
Gly Leu Tyr Ala Arg Gly Gly Leu Ile Leu Glu Pro Arg Ala Leu Ala
                325                 330                 335
Gly Leu Gly Leu Asn Val Ala Leu Ala Leu Ala Gly Leu Gly Leu Tyr
            340                 345                 350
Leu Tyr Ser Gly Leu Asn Thr His Arg Thr His Arg Gly Leu Asn Gly
        355                 360                 365
Leu Pro Arg Leu Glu Val Ala Leu Gly Leu Ala Leu Ala Thr His Arg
    370                 375                 380
Gly Leu Ala Leu Ala Thr His Arg Gly Leu Gly Leu Thr His Arg Gly
385                 390                 395                 400
Leu Tyr Leu Tyr Ser
                405

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 9
acgacagtgt gtgtaaagg                                                    19

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 10
aacatctgtc agcagatctc                                                   20

<210> SEQ ID NO 11
<211> LENGTH: 2804
<212> TYPE: DNA
<213> ORGANISM: Homo sapiens
<220> FEATURE:
<221> NAME/KEY: modified_base
<222> LOCATION: (83)
<223> OTHER INFORMATION: a, t, c, g, other or unknown
<221> NAME/KEY: modified_base
<222> LOCATION: (89)
<223> OTHER INFORMATION: a, t, c, g, other or unknown
<221> NAME/KEY: modified_base
<222> LOCATION: (138)
<223> OTHER INFORMATION: a, t, c, g, other or unknown
<221> NAME/KEY: modified_base
<222> LOCATION: (140)
<223> OTHER INFORMATION: a, t, c, g, other or unknown
<221> NAME/KEY: modified_base
<222> LOCATION: (220)
<223> OTHER INFORMATION: a, t, c, g, other or unknown
<221> NAME/KEY: modified_base
<222> LOCATION: (247)
```

```
<223> OTHER INFORMATION: a, t, c, g, other or unknown
<221> NAME/KEY: modified_base
<222> LOCATION: (456)
<223> OTHER INFORMATION: a, t, c, g, other or unknown
<221> NAME/KEY: modified_base
<222> LOCATION: (463)
<223> OTHER INFORMATION: a, t, c, g, other or unknown
<221> NAME/KEY: modified_base
<222> LOCATION: (553)
<223> OTHER INFORMATION: a, t, c, g, other or unknown
<221> NAME/KEY: modified_base
<222> LOCATION: (555)
<223> OTHER INFORMATION: a, t, c, g, other or unknown
<221> NAME/KEY: modified_base
<222> LOCATION: (570)
<223> OTHER INFORMATION: a, t, c, g, other or unknown
<221> NAME/KEY: modified_base
<222> LOCATION: (577)
<223> OTHER INFORMATION: a, t, c, g, other or unknown
<221> NAME/KEY: modified_base
<222> LOCATION: (580)
<223> OTHER INFORMATION: a, t, c, g, other or unknown
<221> NAME/KEY: modified_base
<222> LOCATION: (602)
<223> OTHER INFORMATION: a, t, c, g, other or unknown
<221> NAME/KEY: modified_base
<222> LOCATION: (612)
<223> OTHER INFORMATION: a, t, c, g, other or unknown
<221> NAME/KEY: modified_base
<222> LOCATION: (671)
<223> OTHER INFORMATION: a, t, c, g, other or unknown
<221> NAME/KEY: modified_base
<222> LOCATION: (690)
<223> OTHER INFORMATION: a, t, c, g, other or unknown
<221> NAME/KEY: modified_base
<222> LOCATION: (695)
<223> OTHER INFORMATION: a, t, c, g, other or unknown
<221> NAME/KEY: modified_base
<222> LOCATION: (697)
<223> OTHER INFORMATION: a, t, c, g, other or unknown
<221> NAME/KEY: modified_base
<222> LOCATION: (704)
<223> OTHER INFORMATION: a, t, c, g, other or unknown
<221> NAME/KEY: modified_base
<222> LOCATION: (711)
<223> OTHER INFORMATION: a, t, c, g, other or unknown
<221> NAME/KEY: modified_base
<222> LOCATION: (869)
<223> OTHER INFORMATION: a, t, c, g, other or unknown
<221> NAME/KEY: modified_base
<222> LOCATION: (1174)
<223> OTHER INFORMATION: a, t, c, g, other or unknown
<221> NAME/KEY: modified_base
<222> LOCATION: (1286)
<223> OTHER INFORMATION: a, t, c, g, other or unknown
<221> NAME/KEY: modified_base
<222> LOCATION: (1720)
<223> OTHER INFORMATION: a, t, c, g, other or unknown
<221> NAME/KEY: modified_base
<222> LOCATION: (1806)
<223> OTHER INFORMATION: a, t, c, g, other or unknown
<221> NAME/KEY: modified_base
<222> LOCATION: (1845)
<223> OTHER INFORMATION: a, t, c, g, other or unknown
<221> NAME/KEY: modified_base
<222> LOCATION: (2002)
<223> OTHER INFORMATION: a, t, c, g, other or unknown
<221> NAME/KEY: modified_base
<222> LOCATION: (2004)
<223> OTHER INFORMATION: a, t, c, g, other or unknown
<221> NAME/KEY: modified_base
<222> LOCATION: (2029)
<223> OTHER INFORMATION: a, t, c, g, other or unknown
<221> NAME/KEY: modified_base
<222> LOCATION: (2042)
<223> OTHER INFORMATION: a, t, c, g, other or unknown
<221> NAME/KEY: modified_base
<222> LOCATION: (2051)
<223> OTHER INFORMATION: a, t, c, g, other or unknown
```

-continued

```
<221> NAME/KEY: modified_base
<222> LOCATION: (2122)
<223> OTHER INFORMATION: a, t, c, g, other or unknown
<221> NAME/KEY: modified_base
<222> LOCATION: (2152)
<223> OTHER INFORMATION: a, t, c, g, other or unknown

<400> SEQUENCE: 11
ccgccgcagc cgccgctcca tccccagccc cggccccgca tccggtttgg aaggggctg       60 caagtttgca aggggcccgg ganaaaaanc gagcagtggc ccttcccgcg tccccagggt     120
ttcaagggac gctaggantn tccgcggccc tggaggttcg cactgggag tggggtgaga      180 tgggggaaa gcgggagggg gctcagggtc cagaagggcn ccgcggtctc gggagtaggg     240
gggcatntgc gtcccgcggg aggggctggg gtgagagtgc ggggccagtg caccggtgcc     300
cgtgtatcgc cctccccagg ccgccaggat ggacgtgttc atgaagggcc tgtccatggc     360
caaggagggc gttgtggcag ccgcggagaa accaagcag ggggtcaccg aggcggcgga     420
gaagaccaag gagggcgtcc tctacgtcgg tgggcngggg gcngggtttc tggggctgca     480
gggctggggg tccccctaca gtgtggagct ggggccgggt cccggggagg ggggttctgg     540
gcaagataat atnantcagc agatggggcn aggtcancan gggtcataag ggacataccc     600
ancccataga ancctgggtc tgtatccgga atgggggaca cggggcgggc tgatgaggtg     660 ggggctcca nctgaaaggc caggaccan tgcantnata aaancacaca ncctcctttt      720
tcttatcttt tttaccatta ttaatagtta tctggtgttg aacactttct gtatgccaag     780
tactgggtaa aatgtcataa catccatttc ctcatgtaat gcttccgccc attctacagg     840
taagggaaac tgggcttccc attggtagnt aaattttagg ttcagaaagg cttgaattga     900
atgtcagttc agccaatttc ttagtggtgg aaccaaactg agttccatcc gtgaaacggg     960
gacaataaca gcaccgcctt cccagggctg gggaaaagtg aagtgcagcg gggcaggcag    1020
aggacttgac acagcactgg ccctcagcca acatccacta gaggggtggg gtatcgcatc    1080
aggtgggaga gaactgcaac ccttgcagac agaggtgtgg ggcccagtgc agtgataaga    1140 cggggttaa catgggggtg caggttgtag gatntgggga cccaaggagg cagtgacggg    1200
gccaggatgc ccactctgta atcaccatgc tgtgctggag tttctgttcc ctcagcgcag    1260
agtccttaaa tgtgccgctt tttctncct gcaggaagca agacccgaga aggtgtggta     1320
caaggtgtgg cttcaggtac tagcccagcc ctggcaccag cccttctctc amttaggcgg    1380
atgatctggc cgggaaccag agggcggggg cggggagac tcccaaggct ctgcgggaa     1440 tgctccgtgg ggagggcagg ccctgggata ctacaaggca gggcatcggt gtttccccct    1500
ggctcccaaa cccccttcctc aaccccctcc ctgctccagt ggctgaaaaa accaaggaac    1560
aggcctcaca tctgggagga gctgtgttct ctggggcagg gaacatcgca gcagccacag    1620
gactggtgaa gagggaggaa ttccctactg atctgaaggt aagcgatcct tctgacccgc    1680
acatgcaggc aaacacacac acacacacac acacacaccn ggcacacaaa taaacctgtc    1740
accatccccg cccccctaat cctgccacca gcttggaaca caagccactt tgcctcccat    1800
cctgcnggcc cgtgctagac tcagctcaga atgcatctga ataaggcgt gcatgggtgt    1860 gacgctcccg gtgatgggga cccagacctg gctgtctgcg tgtatcctgc ttgccagcgt    1920
gacccatatg acttctggcc acgtctgcat gtgtcaatga ttgttcattc atttcttttc    1980
attcaacaaa tatccatgcc ananccagcc ctgtccttga gcttccagnt cccttttcagc   2040 cnaggggagc ntgagggtta ttttggggt ccgatgccc agcacagagc ctgacacaaa     2100
```

```
ggatgaggca taagctggtg antgagtatc caaatggtgg aagtgtggag gntgccaggc    2160
attgggggag cggcgtggag agccagctcc ccaatccatg ctgccacttc aactgtgatt    2220
cgggggaatt tccccttca cctccatccc acttccaagg cactccaaat aaataactga     2280
attagaaatt atccttgttt tgccaaccca ccctagcctt ccccactcca acccacccaa    2340
agcttaccac tgtgggaatt tggggggcat cctggctgtc ctcacgagtc ctgaccttt     2400 ctgcccacag ccagaggaag tggcccagga agctgctgaa gaaccactga ttgagccct     2460 gatggagcca gaaggggaga gttatgagga cccaccccag gaggaatatc aggagtatga    2520
gccagaggcg taggggccca ggagagcccc caccagcagc acaattctgt ccctgtccct    2580
gccccgcccc ccagagccag ggctgtcctt agactccttc tccccaatca cgagatcttc    2640
cttccgctct gaggcaaccc cctcggagcc tgtgttagtg tctgtccatc tgtctgtcct    2700
acccgcccgc gtccaaccccc ggggcatgga cagggccagg gttgcggtcg cggctgggag   2760 cctcgccccct ccagtgttgc ctcctcccat ccagcgtctg cgcg                    2804

<210> SEQ ID NO 12
<211> LENGTH: 223
<212> TYPE: DNA
<213> ORGANISM: Homo sapiens
<220> FEATURE:
<221> NAME/KEY: modified_base
<222> LOCATION: (94)
<223> OTHER INFORMATION: a, t, c, g, other or unknown

<400> SEQUENCE: 12
agggagatcc agctccgtcc tgcctgcagc agcacaaccc tgcacaccca ccatggatgt    60
cttcaagaag ggcttctcca tcgccaagga gggngtggtg ggtgcggtgg aaaagaccaa    120 gcaggggtg acggaagcag ctgagaagac caaggagggg gtcatgtatg tgggattaca    180 ttttttttt aaagaaagaa taaattaatt gtgattaaag ttg                      223

<210> SEQ ID NO 13
<211> LENGTH: 677
<212> TYPE: DNA
<213> ORGANISM: Homo sapiens
<220> FEATURE:
<221> NAME/KEY: modified_base
<222> LOCATION: (7)
<223> OTHER INFORMATION: a, t, c, g, other or unknown
<221> NAME/KEY: modified_base
<222> LOCATION: (28)
<223> OTHER INFORMATION: a, t, c, g, other or unknown
<221> NAME/KEY: modified_base
<222> LOCATION: (34)
<223> OTHER INFORMATION: a, t, c, g, other or unknown
<221> NAME/KEY: modified_base
<222> LOCATION: (36)
<223> OTHER INFORMATION: a, t, c, g, other or unknown
<221> NAME/KEY: modified_base
<222> LOCATION: (51)..(52)
<223> OTHER INFORMATION: a, t, c, g, other or unknown
<221> NAME/KEY: modified_base
<222> LOCATION: (69)
<223> OTHER INFORMATION: a, t, c, g, other or unknown
<221> NAME/KEY: modified_base
<222> LOCATION: (74)
<223> OTHER INFORMATION: a, t, c, g, other or unknown
<221> NAME/KEY: modified_base
<222> LOCATION: (80)..(81)
<223> OTHER INFORMATION: a, t, c, g, other or unknown
<221> NAME/KEY: modified_base
<222> LOCATION: (86)
<223> OTHER INFORMATION: a, t, c, g, other or unknown
<221> NAME/KEY: modified_base
<222> LOCATION: (90)
```

```
<223> OTHER INFORMATION: a, t, c, g, other or unknown
<221> NAME/KEY: modified_base
<222> LOCATION: (94)..(95)
<223> OTHER INFORMATION: a, t, c, g, other or unknown
<221> NAME/KEY: modified_base
<222> LOCATION: (98)
<223> OTHER INFORMATION: a, t, c, g, other or unknown
<221> NAME/KEY: modified_base
<222> LOCATION: (100)
<223> OTHER INFORMATION: a, t, c, g, other or unknown
<221> NAME/KEY: modified_base
<222> LOCATION: (109)..(110)
<223> OTHER INFORMATION: a, t, c, g, other or unknown
<221> NAME/KEY: modified_base
<222> LOCATION: (112)
<223> OTHER INFORMATION: a, t, c, g, other or unknown
<221> NAME/KEY: modified_base
<222> LOCATION: (114)
<223> OTHER INFORMATION: a, t, c, g, other or unknown
<221> NAME/KEY: modified_base
<222> LOCATION: (117)
<223> OTHER INFORMATION: a, t, c, g, other or unknown
<221> NAME/KEY: modified_base
<222> LOCATION: (137)
<223> OTHER INFORMATION: a, t, c, g, other or unknown
<221> NAME/KEY: modified_base
<222> LOCATION: (150)
<223> OTHER INFORMATION: a, t, c, g, other or unknown
<221> NAME/KEY: modified_base
<222> LOCATION: (153)
<223> OTHER INFORMATION: a, t, c, g, other or unknown
<221> NAME/KEY: modified_base
<222> LOCATION: (156)
<223> OTHER INFORMATION: a, t, c, g, other or unknown
<221> NAME/KEY: modified_base
<222> LOCATION: (162)
<223> OTHER INFORMATION: a, t, c, g, other or unknown
<221> NAME/KEY: modified_base
<222> LOCATION: (168)
<223> OTHER INFORMATION: a, t, c, g, other or unknown
<221> NAME/KEY: modified_base
<222> LOCATION: (175)
<223> OTHER INFORMATION: a, t, c, g, other or unknown
<221> NAME/KEY: modified_base
<222> LOCATION: (194)
<223> OTHER INFORMATION: a, t, c, g, other or unknown
<221> NAME/KEY: modified_base
<222> LOCATION: (202)
<223> OTHER INFORMATION: a, t, c, g, other or unknown
<221> NAME/KEY: modified_base
<222> LOCATION: (210)
<223> OTHER INFORMATION: a, t, c, g, other or unknown
<221> NAME/KEY: modified_base
<222> LOCATION: (228)
<223> OTHER INFORMATION: a, t, c, g, other or unknown
<221> NAME/KEY: modified_base
<222> LOCATION: (232)
<223> OTHER INFORMATION: a, t, c, g, other or unknown
<221> NAME/KEY: modified_base
<222> LOCATION: (237)
<223> OTHER INFORMATION: a, t, c, g, other or unknown
<221> NAME/KEY: modified_base
<222> LOCATION: (246)
<223> OTHER INFORMATION: a, t, c, g, other or unknown
<221> NAME/KEY: modified_base
<222> LOCATION: (251)
<223> OTHER INFORMATION: a, t, c, g, other or unknown
<221> NAME/KEY: modified_base
<222> LOCATION: (253)
<223> OTHER INFORMATION: a, t, c, g, other or unknown
<221> NAME/KEY: modified_base
<222> LOCATION: (262)
<223> OTHER INFORMATION: a, t, c, g, other or unknown

<400> SEQUENCE: 13 tttttttnagg ggggaaaaca gggaatanaa aaanangggg gggggttttt nngggggggg      60 ggggaaaaang gttnggggggn naaccnaaan aaanncccnan ggggggggnn antnaanttt   120
```

-continued

```
tgggaaccca aagcccnagg aggattttn gtnaanaacg tnacctcnag tgggncgagg        180
aagaccaagg aaangcccaa cncggttgan cgaggctgtg gtgaacancg tncaacnctg        240
tgcccnccaa nancgtggag gnggcggaga acatcscggt cacctccggg gtggtgcgcm        300
aggaggactt gaggccatct kcccccmac aggagggtgt ggcatccmaa garaaagagg         360
aagtggcaga ggaggcccag agtgggggar actagagggc tacaggccag cgtggatgac        420
ctgaagagcg ctcctctgcc ttggacacca tccctcccta gcacaaggag tgcccgcctt        480
gagtgacatg cggctgccca cgctcctgcc ctcgtcttcc tggccaccct tggcctgtcc        540
acctgtgctg ctgcaccaac ctcactgccc tccctcggcc ccacccaccc tctggtcctt        600
ctgaccccac ttatgctgct gtgaattttt tttttaaatg attccaaata aaacttgagc        660
ccactccaaa aaaaaa                                                        677

<210> SEQ ID NO 14
<211> LENGTH: 1181
<212> TYPE: DNA
<213> ORGANISM: Homo sapiens
<220> FEATURE:
<221> NAME/KEY: modified_base
<222> LOCATION: (130)
<223> OTHER INFORMATION: a, t, c, g, other or unknown
<221> NAME/KEY: modified_base
<222> LOCATION: (140)
<223> OTHER INFORMATION: a, t, c, g, other or unknown
<221> NAME/KEY: modified_base
<222> LOCATION: (172)
<223> OTHER INFORMATION: a, t, c, g, other or unknown
<221> NAME/KEY: modified_base
<222> LOCATION: (193)
<223> OTHER INFORMATION: a, t, c, g, other or unknown
<221> NAME/KEY: modified_base
<222> LOCATION: (329)..(330)
<223> OTHER INFORMATION: a, t, c, g, other or unknown
<221> NAME/KEY: modified_base
<222> LOCATION: (902)
<223> OTHER INFORMATION: a, t, c, g, other or unknown
<221> NAME/KEY: modified_base
<222> LOCATION: (965)
<223> OTHER INFORMATION: a, t, c, g, other or unknown
<221> NAME/KEY: modified_base
<222> LOCATION: (1015)
<223> OTHER INFORMATION: a, t, c, g, other or unknown
<221> NAME/KEY: modified_base
<222> LOCATION: (1159)
<223> OTHER INFORMATION: a, t, c, g, other or unknown

<400> SEQUENCE: 14
aatttcagcg atgcgagggc aaagcgctct cggcggtgcg gtgtgagcca cctcccggcg        60
ctgcctgtct cctccagcag ctccccaagg gataggctct gcccttggtg gtcgaccctc       120
aggccctcgn tctcccaggn cgactctgac gaggggtagg gggtggtccc cnggaggacc       180
cagaggaaag gcnggacaa gaagggaggg aaggggaaa aggaagagg catcatccct          240 agcccaaccg ctcccgatct ccacaagagt gctcgtgacc ctaaacttaa cgtgaggcgc       300
aaaagcgccc caaccttttc ccgccttgnn ccaggcaggc ggctggagtt gatggctcac       360
cccgcgcccc ctgcccatc cccatccgag atagggacga ggagcacgct gcagggaaag        420
cagcgagcgc cggagaggg gcgggcagaa gcgctgacaa atcagcggtg ggggcggaga        480
gccgaggaga aggagaagga ggaggactag gaggaggagg acggcgacga ccagaagggg        540
cccaagagag ggggcgagcg accgagcgcc gcgacgcgaa gtgaggtgcg tgcgggctca       600
gcgcagaccc cggcccggcc cctcctgaga gcgtcctggg cgctccctca cgccttgcct       660
```

| tcaagccttc tgcctttcca ccctcgtgag cggagaactg ggagtggcca ttcgacgaca | 720 |
| ggttagcggg tttgcctccc actccccag cctcgcgtcg ccggctcaca gcggcctcct | 780 |
| ctggggacag tccccccgg gtgcccctcc gcccttcctg tgcgctcctt ttccttcttc | 840 |
| tttcctatta aatattattt gggaattgtt taaatttttt ttttaaaaaa agagagaggc | 900 |
| gnggaggagt cggagttgtg gagaagcaga gggactcagg taagtacctg tggatctaaa | 960 |
| cgggngtctt ttggaaatcc tggagaacgc cggatggaga cgaatggtcg tgggnaccgg | 1020 |
| gaggggtgg tgctgccatg aggaccgctg ggccaggtct ctgggaggtg agtacttgtc | 1080 |
| ctttggggag ctaaggaaag agacttgacc tggctttcgt cctgcttctg atattcccctt | 1140 |
| ctccacaagg gctgagagnt taggctgctt ctccgggatc c | 1181 |

<210> SEQ ID NO 15
<211> LENGTH: 536
<212> TYPE: DNA
<213> ORGANISM: Homo sapiens
<220> FEATURE:
<221> NAME/KEY: modified_base
<222> LOCATION: (422)
<223> OTHER INFORMATION: a, t, c, g, other or unknown
<221> NAME/KEY: modified_base
<222> LOCATION: (481)
<223> OTHER INFORMATION: a, t, c, g, other or unknown
<221> NAME/KEY: modified_base
<222> LOCATION: (490)
<223> OTHER INFORMATION: a, t, c, g, other or unknown
<221> NAME/KEY: modified_base
<222> LOCATION: (525)
<223> OTHER INFORMATION: a, t, c, g, other or unknown

<400> SEQUENCE: 15

| cttaaaagag tctcacactt tggagggttt ctcatgattt ttcagtgttt tttgtttatt | 60 |
| tttccccgaa agttctcatt caaagtgtat tttatgtttt ccagtgtggt gtaaagaaat | 120 |
| tcattagcca tggatgtatt catgaaagga ctttcaaagg ccaaggaggg agttgtggct | 180 |
| gctgctgaga aaccaaaca gggtgtggca gaagcagcag gaaagacaaa agagggtgtt | 240 |
| ctctatgtag gtaggtaaac cccaaatgtc agtttggtgc ttgttcatga gtgatgggtt | 300 |
| aggataacaa tactctaaat gctggtagtt ctctctcttg attcattttt gcatcattgc | 360 |
| ttgtcaaaaa ggtggactga gtcagaggta tgtgtaggta ggtgaatgtg aacgtgtgta | 420 |
| tntgagctaa tagtaaaaat gcgactgttt gcttttcaga ttttttaattt tgcctaatat | 480 |
| ntatgacttn ttaaaatgaa tgtttctgta ctacataatt ctatntcaga gacagt | 536 |

<210> SEQ ID NO 16
<211> LENGTH: 650
<212> TYPE: DNA
<213> ORGANISM: Homo sapiens
<220> FEATURE:
<221> NAME/KEY: modified_base
<222> LOCATION: (214)
<223> OTHER INFORMATION: a, t, c, g, other or unknown
<221> NAME/KEY: modified_base
<222> LOCATION: (476)
<223> OTHER INFORMATION: a, t, c, g, other or unknown

<400> SEQUENCE: 16

| ctgcaggtca acggatctgt ctctagtgct gtacttttaa agcttctaca gttctgaatt | 60 |
| caaaattatc ttctcactgg gccccggtgt tatctcattc ttttttctcc tctgtaagtt | 120 |
| gacatgtgat gtgggaacaa agggataaa gtcattattt tgtgctaaaa tcgtaattgg | 180 |
| agaggacctc ctgttagctg ggctttcttc tatntattgt ggtggttagg agttcctttct | 240 |

```
tctagtttta ggatatatat atatattttt tctttccctg aagatataat aatatatata      300
cttctgaaga ttgagatttt taaattagtt gtattgaaaa ctagctaatc agcaatttaa      360
ggctagcttg agacttatgt cttgaatttg tttttgtagg ctccaaaacc aaggagggag      420
tggtgcatgg tgtggcaaca ggtaagctcc attgtgctta tatcaaagat gatatntaaa      480
gtatctagtg attagtgtgg cccagtatca agattcctat tgaaattgta aaacaatcac      540
tgagcatcta agaacatatc agtcttattg aaactgaatt ctttataaag tatttttaaa      600
taggtaaata ttgattataa ataaaaaata tacttgccaa gaataatgag                 650
```

<210> SEQ ID NO 17
<211> LENGTH: 504
<212> TYPE: DNA
<213> ORGANISM: Homo sapiens
<220> FEATURE:
<221> NAME/KEY: modified_base
<222> LOCATION: (117)
<223> OTHER INFORMATION: a, t, c, g, other or unknown

<400> SEQUENCE: 17

```
atatcttagc caagattcaa tgtttggttg aaccacactc acttgacatc ttggtggctt       60
ttgtttcttc tgaccactca gttatctatg catgtgtag atacaggtgt atggaancga      120
tggctagtgg aagtggaatg atttttaagtc actgttattc taccacccttt taatctgttg     180 ttgctctttta tttgtaccag tggctgagaa gaccaaagag caagtgacaa atgttggagg     240
agcagtggtg acgggtgtga cagcagtagc ccagaagaca gtggagggag cagggagcat     300
tgcagcagcc actggctttg tcaaaaagga ccagttgggc aaggtatggc tgtgtacgtt     360
ttgtgttaca tttataagct ggtgagatta cggttcattt tcatgtgaag cctgaggca      420 ggagcaagat acttactgtg gggaacggct acctgaccct ccccttgtga aaaagtgcta     480
cctttatatt ggtcttgctt gttt                                             504
```

<210> SEQ ID NO 18
<211> LENGTH: 726
<212> TYPE: DNA
<213> ORGANISM: Homo sapiens
<220> FEATURE:
<221> NAME/KEY: modified_base
<222> LOCATION: (553)
<223> OTHER INFORMATION: a, t, c, g, other or unknown

<400> SEQUENCE: 18

```
aaaagtttac atactttgag gttgataacc catgttgccg caatgtttcc ccggaggcat       60
tgtggagttt agaatgccag tagtaatatt aaggtgtgcc attttcaaga tccgtggcca      120
acatccctat atgtaagatt tttccaaaac atggttctga ttttaaaag tgaaaatgc      180 tacttcatca tgttcttttt gtgcttctta ctttaaatat tagaatgaag aaggagcccc     240
acaggaagga attctggaag atatgcctgt ggatcctgac aatgaggctt atgaaatgcc     300
ttctgaggta ggagtccaag ctgaatcttt ctaacaagac agtaccaaaa acctgtcatt     360
gtcacatttc tctttcatta gtgcttagtg agaatcattt gctctctaca tgctcattag     420
tggacaactt gcaagttaag aatagttttt acatttttaa agggtccttta aaaaaaaga     480 ggaggaggaa gatgaagaag aggaagaaag gatgtaaaag aaatcatatg tagtccacat     540
agcttaatat acntactact tgacccttta caggaaaagc tttactaacc cctgcattag     600
agaatatatt tttttgcaaa aacattgatt gtaaattta gtgtaaagtg gggagccatt      660
```

```
tcctatctca ttggctgtcc agtgctgatg cgtaattgaa acttatacta acagtgtgtg      720
ctgtct                                                                 726

<210> SEQ ID NO 19
<211> LENGTH: 1596
<212> TYPE: DNA
<213> ORGANISM: Homo sapiens
<220> FEATURE:
<221> NAME/KEY: modified_base
<222> LOCATION: (415)
<223> OTHER INFORMATION: a, t, c, g, other or unknown
<221> NAME/KEY: modified_base
<222> LOCATION: (486)
<223> OTHER INFORMATION: a, t, c, g, other or unknown
<221> NAME/KEY: modified_base
<222> LOCATION: (585)
<223> OTHER INFORMATION: a, t, c, g, other or unknown
<221> NAME/KEY: modified_base
<222> LOCATION: (1119)
<223> OTHER INFORMATION: a, t, c, g, other or unknown
<221> NAME/KEY: modified_base
<222> LOCATION: (1419)
<223> OTHER INFORMATION: a, t, c, g, other or unknown
<221> NAME/KEY: modified_base
<222> LOCATION: (1503)
<223> OTHER INFORMATION: a, t, c, g, other or unknown
<221> NAME/KEY: modified_base
<222> LOCATION: (1549)
<223> OTHER INFORMATION: a, t, c, g, other or unknown
<221> NAME/KEY: modified_base
<222> LOCATION: (1554)
<223> OTHER INFORMATION: a, t, c, g, other or unknown
<221> NAME/KEY: modified_base
<222> LOCATION: (1561)
<223> OTHER INFORMATION: a, t, c, g, other or unknown
<221> NAME/KEY: modified_base
<222> LOCATION: (1581)
<223> OTHER INFORMATION: a, t, c, g, other or unknown
<221> NAME/KEY: modified_base
<222> LOCATION: (1589)
<223> OTHER INFORMATION: a, t, c, g, other or unknown

<400> SEQUENCE: 19
ttttgatttt tctaatatta ggaagggtat caagactacg aacctgaagc ctaagaaata       60
tctttgctcc cagtttcttg agatctgctg acagatgttc catcctgtac aagtgctcag      120
ttccaatgtg cccagtcatg acatttctca aagttttttac agtgtatctc gaagtcttcc     180
atcagcagtg attgaagcat ctgtacctgc ccccactcag catttcggtg cttcccttttc    240 actgaagtga atacatggta gcagggtctt tgtgtgctgt ggattttgtg gcttcaatct     300
acgatgttaa aacaaattaa aaacacctaa gtgactacca cttatttcta aatcctcact     360 attttttttgt tgctgttgtt cagaagttgt tagtgatttg ctatcatata ttatnagatt    420
tttaggtgtc ttttaatgat actgtctaag aataatgacg tattgtgaaa tttgttaata    480
tatatnatac ttaaaaatat gtgagcatga aactatgcac ctataatact aaatatgaaa   540
ttttaccatt ttgcgatgtg ttttattcac ttgtgtttgt atatnaatgg tgagaattaa    600
aataaaacgt tatctcattg caaaaatatt ttatttttat cccatctcac tttaataata     660
aaaatcatgc ttataagcaa catgaattaa gaactgacac aaaggacaaa aatataaagt     720
tattaatagc catttgaaga aggaggaatt ttagaagagg tagagaaaat ggaacattaa     780
ccctacactc ggaattccct gaagcaacac tgccagaagt gtgttttggt atgcactggt     840
tccttaagtg gctgtgatta attattgaaa gtggggtgtt gaagaccccca actactattg    900 tagagtggtc tatttctccc ttcaatcctg tcaatgtttg ctttacgtat tttgggggaac   960 tgttgtttga tgtgtatgtg tttataattg ttatacattt ttaattgagc cttttattaa   1020
```

```
catatattgt tattttttgtc tcgaaataat tttttagtta aaatctatttt tgtctgatat    1080 tggtgtgaat gctgtaccttt tctgacaata aataatatnc gaccatgaat aaaaaaaaaa    1140
aaaaagtggg ttcccgggaa ctaagcagtg tagaagatga ttttgactac accctcctta    1200
gagagccata agacacatta gcacatatta gcacattcaa ggctctgaga gaatgtggtt    1260
aactttgttt aactcagcat tcctcacttt tttttttaa tcatcagaaa ttctctctct     1320
ctctctcttt ttctctcgct ctctttttt tttttttttt ttttacagga aatgccttta    1380
aacatcgttg ggaactacca gagtcacctt aaagggagna tcaattctct aggactggat    1440
aaaaatttca tgggcctcct ttaaaatgtt gcccaaatat atggaattct aggggttttt    1500
ccntaggggg aagggttttt tctcttttcn ggggaggatc cttttaacnc cccngggggg    1560
ngcccggaaa ataaacttgg ngggggggna aaactt                              1596

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 20
atgtcttcaa gaagggcttc                                                  20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 21
ccttggtctt ctcagctgct                                                  20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 22
agcgtggatg acctgaagag                                                  20

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 23
agcacaggtg gacaggccaa g                                                21

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 24
```

```
gatatgttct tagatgctca g                                              21

<210> SEQ ID NO 25
<211> LENGTH: 14
<212> TYPE: PRT
<213> ORGANISM: Homo sapiens

<400> SEQUENCE: 25

Gly Ser Lys Thr Lys Glu Gly Val Val His Gly Val Thr Thr
 1               5                  10
```